(12) United States Patent
Cotten et al.

(10) Patent No.: US 6,841,158 B1
(45) Date of Patent: *Jan. 11, 2005

(54) RECOMBINANT CELO VIRUS AND CELO VIRUS DNA

(75) Inventors: Matthew Cotten, Vienna (AT); Anne-Isabelle Michou, Basel (CH); Gerhard Christofori, Vienna (AT); Amelia Compagni, Vienna (AU)

(73) Assignee: Boehringer Ingelheim International GmbH, Ingelheim am Rhein (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 09/399,778

(22) Filed: Sep. 21, 1999

Related U.S. Application Data
(60) Provisional application No. 60/104,895, filed on Oct. 20, 1998.

(30) Foreign Application Priority Data

Sep. 22, 1998 (EP) .............................................. 98117900

(51) Int. Cl.⁷ ...................... H61K 39/235; H61K 39/29; H61K 39/00; H61K 39/12; C12N 7/01; C12P 21/06; C07H 21/04

(52) U.S. Cl. ................................ 424/233.1; 424/184.1; 424/199.1; 424/202.1; 435/69.1; 435/235.1; 536/23.72

(58) Field of Search ............................. 536/23.1, 23.72, 536/23.4; 435/320.1, 69.1, 235.1; 424/93.1, 202.1, 184.1, 199.1, 233.13; 514/21

(56) References Cited

U.S. PATENT DOCUMENTS 4,491,589 A * 1/1985 Dell et al. ................... 514/400
6,335,016 B1 * 1/2002 Baker et al. ............. 424/199.1

FOREIGN PATENT DOCUMENTS

SU      1490962      * 6/1987
WO      WO 97/40180  * 10/1997

OTHER PUBLICATIONS

Michou et al. (Journal of Virology. 1999; 73 (2): 1399–1410.*
Nishiaka et al, Journal of Surigcal Research, vol. 38, pg. 592–598, 1985 (AG).*
Seidal et al, American Journal of Physiol., vol. 249, pg. G–434–38, 1985.*
Baker, A., et al., "Polyethylenimine (PEI) is a simple, inexpensive and effective reagent for condensing and linking plasmid DNA to adneovirus for gene delivery," *Gene Ther.* 4:773–782 (Aug. 1997).*

Bett, A.J., et al., "An efficient and flexible system for construction of adenovirus vectors with insertions or deletions in early regions 1 and 3," *Proc. Natl. Acad. Sci. USA* 91:8802–8806 (Sep. 1994).*
Boussif, O., et al., "A versatile vector for gene and oligonucleotide transfer into cells in culture and in vivo: Polyethylenimine," *Proc. Natl. Acad. Sci. USA* 92:7297–7310 (Aug. 1995).*
Buge, S.L., et al., "An Adenovirus–Simian Immunodeficiency Virus env Vaccine Elicits Humoral, Cellular, and Mucosal Immune Responses in Rhesus Macaques and Decreases Viral Burden following Vaginal Challenge," *J. Virol.* 71:8531–8541 (Nov. 1997).
Caravokyri, C., and Leppard, K.N., "Constitutive Episomal Expression of Polypeptide IX (pIX) in a 293–Based Cell Line Complements the Deficiency of pIX Mutant Adenovirus type 5," *J. Virol.* 69:6627–6633 (Nov. 1995).
Celli, G., et al., "Soluble dominant–negative receptor uncovers essential roles for fibroblast growth factors in multi–organ induction and patterning," *EMBO J.* 17:1642–1655 (Mar. 1998).
Chartier, C., et al., "Efficient Generation of Recombinant Adenovirus Vectors by Homologous Recombination in *Escherichia coli*," *J. Virol.* 70:4805–4810 (Jul. 1996).
Chiocca, S., et al., "The Complete DNA Sequence and Genomic Organization of the Avian Adenovirus CELO," *J. Virol.* 70:2939–2949 (May 1996).
Chiocca, S., et al., "Identification of a Novel Antiapoptotic Protein, GAM–1, Encoded by the CELO Adenovirs," *J. Virol.* 71:3168–3177 (Apr. 1997).
Colby, W.W., and Shenk, T., "Adenovirus Type 5 Virions Can be Assembled In Vivo in the Absence of Detectable Polypeptide IX," *J. Virol.* 39:977–980 (Sep. 1981).
Cotten, M., et al., "Chicken Adenovirus (CELO Virus) Particles Augment Receptor–Mediated DNA Delivery to Mammalian Cells and Yield Exceptional Levels of Stable Transformants," *J. Virol.* 67:3777–3785 (Jul. 1993).
Cowen, B., et al., "Avian Adenoviruses: Effect on Egg Production, Shell Quality, and Feed Consumption," *Avian Diseases* 22:459–470 (Jul.–Sep. 1978).
Crouzet, J., et al., "Recombinational construction in *Escherichia coli* of infectious adenoviral genomes," *Proc. Natl. Acad. Sci. USA* 94:1414–1419 (Feb. 1997).

(List continued on next page.)

Primary Examiner—James Housel
Assistant Examiner—Shannon Foley
(74) Attorney, Agent, or Firm—Sterne, Kessler, Goldstein & Fox P.L.L.C.

(57) ABSTRACT

Recombinant CELO virus or CELO virus DNA with a deletion at the right end of the viral genome that allows insertion of large pieces of foreign DNA. The virus is useful as a vaccine for animals, in particular birds, and for gene therapy and vaccine applications in humans. The virus can also be used for recombinant protein production.

56 Claims, 21 Drawing Sheets

DeGregori, J., et al., "Distinct roles for E2F proteins in cell growth control and apoptosis," *Proc. Natl. Acad. Sci. USA* 94:7245–7250 (Jul. 1997).

Degryse, E., "In vivo intermolecular recombination in *Escherichia coli*: application to plasmid constructions," *Gene* 170:45–50 (Apr. 1996).

de Wet, J.R., et al., "Firefly Luciferase Gene: Structure and Expression in Mammalian Cells," *Mol. Cell. Biol.* 7:725–737 (Feb. 1987).

Fisher, K. J., et al., "Recombinant Adenovirus Deleted of All Viral Genes for Gene Therapy of Cystic Fibrosis," *Virol.* 217:11–22 (Mar. 1996).

Gerber, H.-P., et al., "VEGF is required for growth and survival in neonatal mice," *Develop.* 126:1149–1159 (Mar. 1999).

Gerdts, V., et al., "Protection of Pigs against Aujeszky's disease by DNA vaccination," *J. Gen. Virol.* 78:2139–2146 (Sep. 1997).

Ghosh–Choudhury, G., et al., "Protein IX, a minor component of the human adenovirus capsid, is essential for the packaging of full length genomes," *EMBO J.* 6:1733–1739 (Jun. 1987).

Gluzman, Y., et al., "Helper–free Adenovirus Type–5 Vectors," in *Eukaryotic Viral Vectors*, Gluzman, Y., ed., Cold Spring Harbor Laboratory, Cold Spring Harbor, NY, pp. 187–192 (1982).

Graham, F.L., and Smiley, J., "Characteristics of a Human Cell Line Transformed by DNA from Human Adenovirus Type 5," *J. Gen. Virol.* 36:59–72 (Jul. 1977).

Grubb, B.R., et al., "Inefficient gene transfer by adenovirus vector to cystic fibrosis airway epithelia of mice and humans," *Nature* 371:802–806 (Oct. 1994).

Hardy, S., et al., "Construction of Adenovirus Vectors through Cre–lox Recombination," *J. Virol.* 71:1842–1849 (Mar. 1997).

Havenga, M.J. E., et al., "Second gene expression in bicistronic constructs using short synthetic intercistrons and viral IRES sequences," *Gene* 222:319–327 (Nov. 1998).

Hay, R.T., et al., "Replication of Adenovirus Mini–chromosomes," *J. Mol. Biol.* 175:493–510 (Jun. 1984).

He, T.–C., et al., "A simplified system for generating recombinant adenoviruses," *Proc. Natl. Acad. Sci. USA* 95:2509–2514 (Mar. 1998).

Hess, M., et al., "The Avian Adenovirus Penton: Two Fibres and One Base," *J. Mol. Biol.* 252:379–385 (Sep. 1995).

Horwitz, M.S., "Adenoviruses," in *Fields Virology*, Third Edition, Fields, B.N., et al., eds., Lippincott–Raven Publishers, Philadelphia, PA, pp. 2149–2171 (1996).

Imler, J.–L., et al., "An efficient procedure to select and recover recombinant adenovirus vectors," *Gene Ther.* 2:263–268 (Jun. 1995).

Kawaguchi, T., et al., "Establishment and Characterization of a Chicken Hepatocellular Carcinoma Cell Line, LMH," *Cancer Res.* 47:4460–4464 (Aug. 1987).

Karlsson, S., et al., "Transfer of genes into hematopoietic cells using recombinant DNA viruses," *Proc. Natl. Acad. Sci. USA* 82:158–162 (Jan. 1985).

Khatri, A., et al., "Gene Expression by Atypical Recombinant Ovine Adenovirus Vectors during Abortive Infection of Human and Animal Cells in Vitro," *Virol.* 239:226–237 (Dec. 1997).

Klonjkowski, B., et al., "A Recombinant E1–Deleted Canine Adenoviral Vector Capable of Transduction and Expression of a Transgene in Human–Derived Cells and In Vivo," *Human Gene Ther.* 8:2103–2115 (Nov. 1997).

Kovesdi, I., et al., "Adenoviral vectors for gene transfer," *Curr. Opin. Biotechnol.* 8:583–589 (Oct. 1997).

Kumar–Singh, R., and Chamberlain, J.S., "Encapsidated adenovirus minichromosomes allow delivery and expression of a 14 kb dystrophin cDNA to muscle cells," *Human Mol. Genet.* 5:913–921 (Jul. 1996).

Lasher, H.N., and Davis, V.S., "History of Infectious Bursal Disease in the U.S.A.–The First Two Decades," *Avian Diseases* 41:11–19 (Jan.–Mar. 1997).

Laver, W.G., et al., "Purification and Properties of Chick Embryo Lethal Orphan Virus (an Avian Adenovirus)," *Virol.* 45:598–614 (Sep. 1971).

Lemay, P., et al., "Human Adenovirus Type 2 Protein IIIa," *Virol.* 101:131–143 (Feb. 1980).

Levenson, V.V., et al., "Internal Ribosomal Entry Site–Containing Retroviral Vectors with Green Fluorescent Protein and Drug Resistance Markers," *Human Gene Ther.* 9:1233–1236 (May 1998).

Li, P., et al., "The Structural Proteins of Chick Embryo Lethal Orphan Virus (Fowl Adenovirus type 1)," *J. Gen. Virol.* 65:1803–1815 (Oct. 1984).

Li, P., et al., "DNA–binding Proteins of Chick Embryo Lethal Orphan Virus: Lack of Complementation between Early Proteins of Avian and Human Adenoviruses," *J. Gen. Virol.* 65:1817–1825 (Oct. 1984).

Li, P., et al., "Structural Organization and Polypeptide Composition of the Avian Adenovirus Core," *J. Virol.* 52:638–649 (Nov. 1984).

Li, X., et al., "Dicistronic LacZ and Alkaline Phosphatase Reporter Constructs Permit Simultaneous Histological Analysis of Expression from Multiple Transgenes," *BioTechniques* 23:874–882 (Nov. 1997).

Lieber, A., et al., "Recombinant Adenoviruses with Large Deletions Generated by Cre–Mediated Excision Exhibit Different Biological Properties Compared with First–Generation Vectors In Vitro and In Vivo," *J. Virol.* 70:8944–8960 (Dec. 1996).

Lillehoj, H.S., and Trout, J.M., "Avian Gut–Associated Lymphoid Tissues and Intestinal Immune Responses to Eimeria Parasites," *Clin. Microbiol. Rev.* 9:349–360 (Jul. 1996).

López de Quinto, S., and Martinez–Salas, E., "Parameters influencing translational efficiency in aphthovirus IRES–based bicistronic expression vectors," *Gene* 217:51–56 (Sep. 1998).

Lubeck, M.D., et al., "Long–term protection of chimpanzees against high–dose HIV–1 challenge induced by immunization," *Nature Med.* 3:651–658 (Jun. 1997)..

McFerran, J.B., and Adair, B. McC., "Avian Adenoviruses—A Review, " *Avian Pathol.* 6:189–217 (1977).

Mittal, S.K., et al., "Development of a bovine adenovirus type 3–based expression vector," *J. Gen. Virol.* 76:93–102 (Jan. 1995).

Miyake, S., et al., "Efficient generation of recombinant adenoviruses using adenovirus DNA–terminal protein complex and a cosmid bearing the full–length virus genome," *Proc. Natl. Acad. Sci. USA* 93:1320–1324 (Feb. 1996).

Oliner, J.D., et al., "In vivo cloning of PCR products in *E. coli*," *Nucl. Acids Res.* 21:5192–5197 (Nov. 1993).

Parks, R.J., et al., "A helper–dependent adenovirus vector system: Removal of helper virus by Cre–mediated excision of the viral packaging signal," *Proc. Natl. Acad. Sci. USA* 93:13565–13570 (Nov. 1996).

Pettersson, U., and Roberts, R.J., "Adenovirus Gene Expression and Replication: A Historical Review," in *DNA Tumor Viruses,* Cold Spring Harbor Laboratory, Cold Spring Harbor, NY, pp. 37–57 (1986).

Plank, C., et al., "Gene Transfer into Hepatocytes Using Asialoglycoprotein Receptor Mediated Endocytosis of DNA Complexed with an Artificial Tetra–Antennary Galactose Ligand," *Bioconjugate Chem. 3:*533–539 (Nov./Dec. 1992).

Polyak, K., et al., "A model of p53–induced apoptosis," *Nature 389:*300–305 (Sep. 1997).

Robbins, A.K., et al., "Characterization of a Pseudorabies Virus Glycoprotein Gene with Homology to Herpes Simplex Virus Type 1 and Type 2 Glycoprotein C," *J. Virol. 58:*339–347 (May 1986).

Schaack, J., et al., "Efficient Selection of Recombinant Adenoviruses by Vectors That Express β–Galactosidase," *J. Virol. 69:*3920–3923 (Jun. 1995).

Schreurs, C., et al., "Glycoprotein gIII of Pseudorabies Virus Is Multifunctional," *J. Virol. 62:*2251–2257 (Jul. 1988).

Shenk, T., "Group C Adenoviruses as Vectors for Gene Therapy," in *Viral Vectors: Gene Therapy and Neuroscience Applications,* Kaplitt, M.G. and Loewy, A.D., eds., Academic Press, San Diego, CA, pp. 43–54 (1995).

Shenk, T., "Adenoviridae: The Viruses and Their Replication," in *Fields Virology,* Third Eidtion, Fields, B.N., et al., eds., Lippincott–Raven Publsihers, Philadelphia, PA, pp. 2111–2148 (1996).

Shirley, M.W., "Research on Avian Coccidia: An Update," *Br. Vet. J. 148:*479–499 (Nov./Dec. 1992).

Soberon, X., et al., "Construction and Characterization of New Cloning Vehicles: IV. Deletion Derivatives of pBR322 and pBR325," *Gene 9:*287–305 (May 1980).

Talsma, H., et al., "Stabilization of gene delivery systems by freeze–drying," *Int. J. Pharmaceutics 157:*233–238 (Nov. 1997).

Taylor, M.A., and Catchpole, J., "Coccidiosis of domestic ruminants," *Appl. Parasitol. 35:*73–86 (Jun. 1994).

Van Doren, K., et al., "Infection of Eucaryotic Cells by Helper–Independent Recombinant Adenoviruses: Early Region 1 Is Not Obligatory for Integration of Viral DNA," *J. Virol. 50:*606–614 (May 1984).

Vermeulen, A.N., "Progress in recombinant vaccine development against coccidiosis. A review and prospects into the new millennium," *Intl. J. Parasitol. 28:*1121–1130 (Jul. 1998).

Vrati, S., et al., "Construction and Transfection of Ovine Adenovirus Genomic Clones to Rescue Modified Viruses," *Virol. 220:*200–203 (Jun. 1996).

Weiss, R.S., et al., "Human Adenovirus Early Region 4 Open Reading Frame 1 Genes Encode Growth–Transforming Proteins That May Be Distantly Related to dUTP Pyrophosphatase Enzymes," *J. Virol. 71:*1857–1870 (Mar. 1997).

Wilson, C., and Kay, M.A., "Immunomodulation to enhance gene therapy," *Nature Med. 1:*887–889 (Sep. 1995).

Xu, Z.Z., et al., "Construction of Ovine Adenovirus Recombinants by Gene Insertion or Deletion of Related Terminal Region Sequences," *Virol. 230:*62–71 (Mar. 1997).

Yates, V.J., and Fry, D.E. "Observations on a Chicken Embryo Lethal Orphan (CELO) Virus," *Am. J. Vet. Res. 18:*657–660 (Jul. 1957).

Zabner, J., et al., "Adenovirus–Mediated Gene Transfer to Ciliated Airway Epithelia Requires Prolonged Incubation Time," *J. Virol. 70:*6994–7003 (Oct. 1996).

Zabner, J., et al., "Lack of High Affinity Fiber Receptor Activity Explains the Resistance of Ciliated Airway Epithelia to Adenovirus Infection," *J. Clin. Investig. 100:*1144–1149 (Sep. 1997).

Zheng, B., et al., "The E1 sequence of bovine adenovirus type 3 and complementation of human adenovirus type 5 E1A function in bovine cells," *Virus Res. 31:*163–186 (Feb. 1994).

Complete English language translation for WO 97/40180.

NCBI Entrez, GenBank Report, Accession No. U46933, from Chiocca, S., et al. (Jun. 1996).

NCBI Entrez, GenBank Report, Accession No. L08856, from Gilbert, W. (Jul. 1993).

* cited by examiner

Fig. 1 A
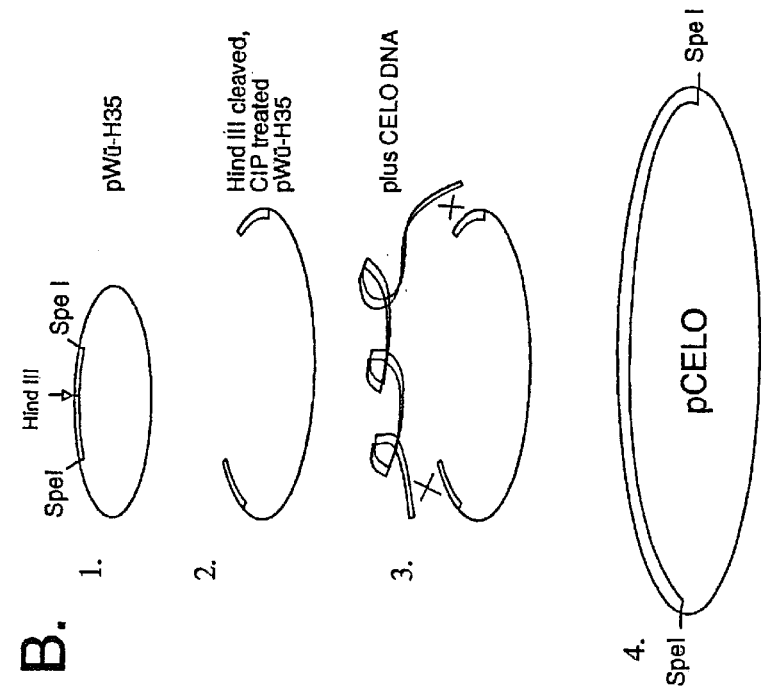
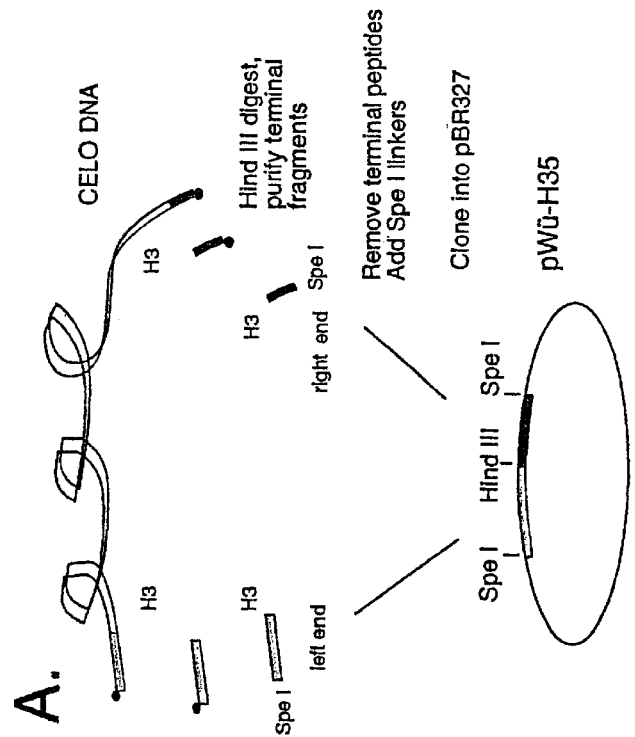

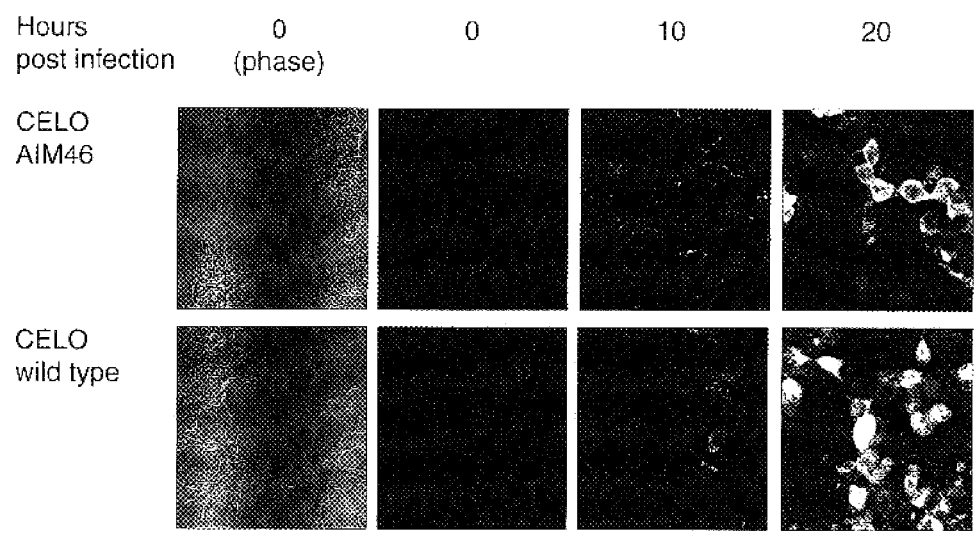
Fig. 5/1

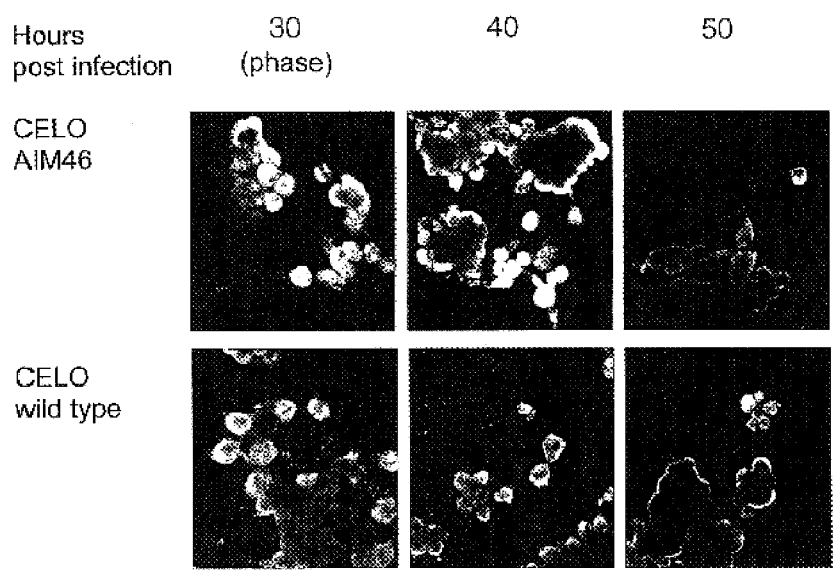
Fig. 5/2

Fig. 6
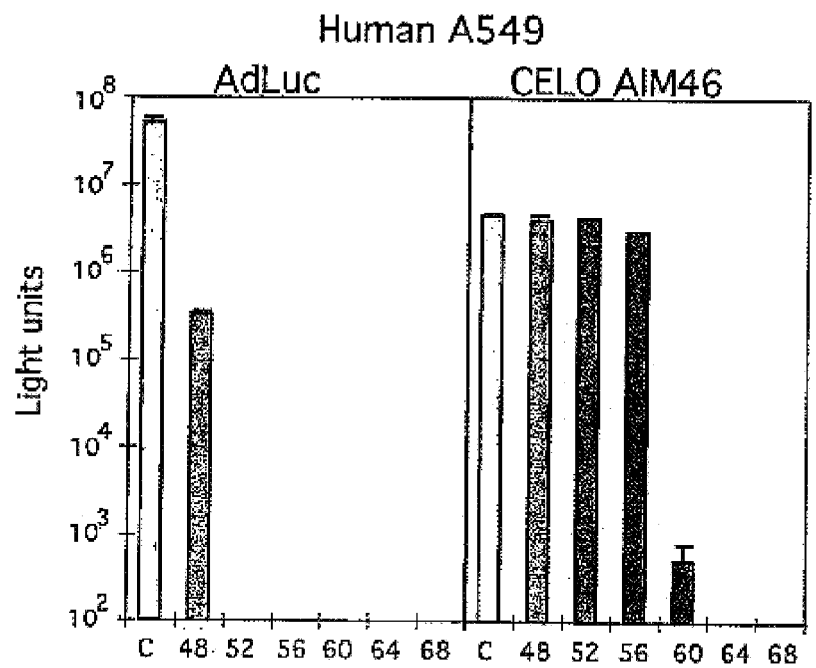
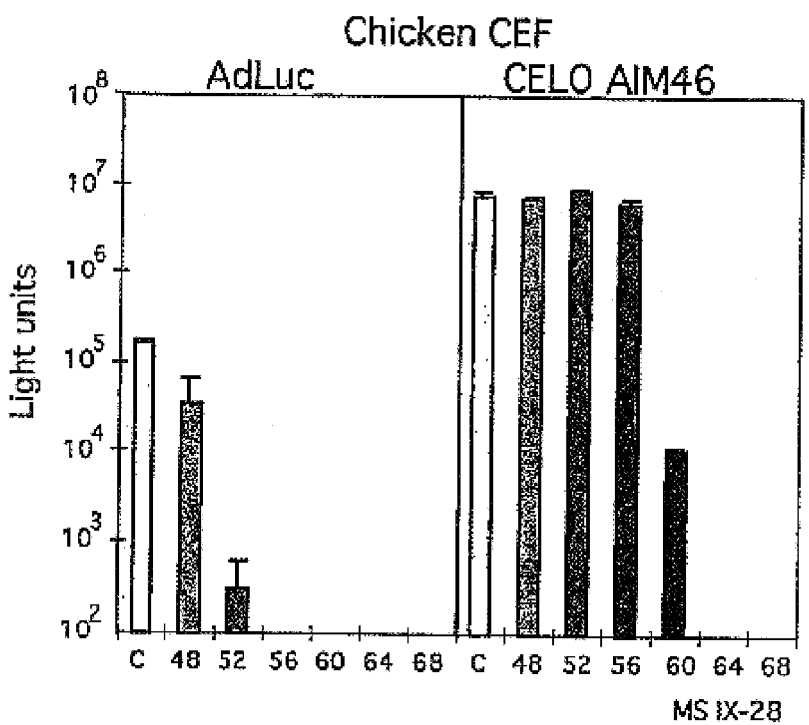

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:

-continued

```
<221> NAME/KEY: misc_feature
<222> LOCATION: (1)..(20)
<223> OTHER INFORMATION: Synthetic DNA

<400> SEQUENCE: 1
ccgagaatcc accaatcgta                                              20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic DNA

<400> SEQUENCE: 2
cagcgtgtcg ctatacgcaa                                              20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic DNA

<400> SEQUENCE: 3
gcgatgacga aattcttagc                                              20
```

RECOMBINANT CELO VIRUS AND CELO VIRUS DNA

This application claims the benefit of U.S. Provisional Application No. 60/104,895, filed Oct. 20, 1998.

The present invention relates to viral vectors and viral DNA.

Adenovirus has been studied for its role in human disease (25), as a model for many important discoveries in molecular biology, including mRNA splicing, DNA replication, transcription and cell transformation (reviewed in 44) and more recently as a powerful reagent for transient gene expression (12, 46). A detailed understanding of the adenoviral life cycle is well established (reviewed in 50). Since the initial efforts to use adenovirus as a gene transfer vector (18, 52, 28) the virus has gained in popularity as a vector and a number of methods of generating alterations in the viral genome to carry novel genes have been developed (2, 5, 11, 15, 21, 23, 26, 32, 38, 41, 43, 48 reviewed in 31, 49). Because of the ease of vector construction and purification, and because these vectors have a potent ability to transiently transduce novel genetic material into a variety of mammalian cell types in vivo, adenovirus vectors were used extensively in early efforts at clinical gene therapy.

Unfortunately, several features of the adenovirus type 5 (Ad5) based vectors initially used have limited the success in the initial applications. These included both the host immune response to adenovirus (reviewed in ref. 55) as well as the failure of the virus to efficiently enter certain target cell types (20, 58, 59). Thus, there is now an interest in adenovirus types that could provoke less aggressive host immune responses and could enter target cells with greater efficiency.

A large number of alternate adenovirus serotypes are known and may provide advantages in some applications over Ad5-based vectors. Additional adenoviruses that have recently been modified as vectors include the ovine adenovirus 287 (29, 53, 56,), the bovine adenovirus type 3 (40, 60), and the canine adenovirus (30). It is considered that these alternate serotypes would provide both a novel vector backbone to which there is no pre-existing immune response in the target host. Furthermore, because adenoviruses are extremely species specific in their replication capacity (50) a degree of security against inappropriate vector replication is gained by using an vector derived from a distant species of adenovirus.

There are several justifications for pursuing these alternate viral subtypes. For vaccine applications in their non-human hosts, these viruses, if properly modified, may provoke more effective immune responses than a human adenovirus based vector. Furthermore, more robust immune responses might be expected from a replication competent virus; thus a vector is most useful in a host where replication is partially or fully permissive. This is not the case with human adenovirus based vectors in nearly all nonhuman hosts.

It has been an object of the invention to provide an alternative adenovirus vector for use as a gene delivery vector and for use as a vaccine.

To solve the problem underlying the present invention, the avian adenovirus CELO has been chosen to be modified. CELO (chicken embryo lethal orphan or fowl adenovirus type 1, reviewed in 39) was characterized as an infectious agent in 1957 (57). There are few serious health or economic consequences of CELO virus infection. CELO can be isolated from healthy chickens and in general, do not cause disease when experimentally re-introduced into chickens (10).

CELO virus is structurally similar to the mammalian adenoviruses (mastadenoviruses) with an icosahedral capsid of 70–80 nm made up of hexon and penton structures (33); the CELO virus genome is a linear, double-stranded DNA molecule with the DNA condensed within the virion by virus-encoded core proteins (33, 36). CELO virus has a larger genome than Ad5 (44 kb vs. ca. 36kb, ref. 6, WO 97/40180). The CELO virion has two fibers of different lengths at each vertex (24, 33, 35) rather than the single fiber of most other serotypes (reviewed in 50). The CELO virus is not able to complement the E1A functions of Ad5 and CELO virus replication is not facilitated by Ad5 E1 activity (37). The complete DNA sequence of CELO (6, WO 97/40180) revealed additional differences between CELO virus and the mastadenoviruses including the absence of sequences corresponding to the Ad5 early regions E1A, E1B, E3 and E4. The CELO genome contains approximately 5 kb of sequence at the left end and 12 kb at the right end, rich in open reading frames, which have no sequence homology to Ad5 but probably encode the early functions of the virus.

When developing CELO into a gene delivery vector, it has been considered that the virus is naturally defective in mammalian cells and this property should limit the possibility of complementation by wildtype mammalian adenovirus. The CELO virion has increased DNA packaging capacity and much greater physical stability than the virion of Ad5. One practical feature of CELO is the ability to grow the virus in chicken embryos, a system of low cost and high convenience (9, 33).

In the experiments of the present invention, the frontier sequences of CELO, i.e. the leftmost 5 kb and rightmost 13 kb of the CELO genome that are largely unexplored and are not common to other adenoviruses, have been examined. Viral genetics have been used to characterize requirements for these left and right end CELO sequences in virus replication. Viral sequences have been deleted in discrete steps in order to identify the regions essential or non essential for replication. To facilitate monitoring the replication of the mutants, a luciferase expression cassette was inserted in place of the deleted sequences. The modified CELO genomes were engineered as bacterial plasmids using homologous recombination in E. coli (5). Subsequently, after their release from the plasmid backbone by enzymatic digestion, the viral genomes were transfected into a chicken cell line supporting wildtype CELO replication. Transfection of the large viral DNA molecules (about 50 kb) was facilitated by optimizing the polyethyleneimine (PEI) mediated transfection method (1, 3). Furthermore, with all mutations, a second transfection was performed with a plasmid bearing the CELO sequences that were deleted from the mutant to determine if the mutation could be complemented. Monitoring the production of luciferase in cells treated with lysates of the initial transfectants allowed us to determine if virus replication and production of transducing viral particles had occurred. These strategies were used to determine the essential portions of both left and right frontier sequence. As anticipated, some of the sequences were required in cis and presumably these contain packaging signals, transcriptional promoters or other transcription signals.

The present invention relates to recombinant CELO virus and CELO virus DNA that have the region spanning nucleotides 41731–43684 of the CELO wild type virus genome completely or partially deleted and/or contain an insertion in this region.

This CELO virus (DNA) and its derivatives have been designated CELO AIM46 or CELO AIM46 derivatives, respectively.

In an embodiment, the invention is directed to a CELO AIM46 derivative with an complete or partial deletion and/or insertion within the region nt 41523–43684.

In a further embodiment, the invention is directed to a CELO AIM46 derivative with an complete or partial deletion and/or insertion within the region nt 41002–43684.

In a further embodiment, the invention is directed to a CELO AIM46 derivative with a complete or partial deletion and/or insertion within the region nt 40065–43684.

Preferably, the regions defined above are completely deleted to provide more space for inserting the foreign DNA in place of the deletion.

The modified viruses of the invention, which are derived from CELO virus, contain deletions and/or insertions at the right end of the genome, are replication competent and can carry at least 3.2 kb more DNA than the wildtype genome.

More specifically, the CELO virus and CELO virus DNA of the invention carry a deletion of wild type CELO sequences for insertion of an expression cassette for foreign genes in the CELO virus genome, the deletion spanning approximately the region from nt 40,000 to approximately within 200 bp of the right terminus of the virus genome. The region that may be completely or partially deleted or disrupted is thus defined by the last three rightward open reading frames encoding peptides of greater than 99 amino acid residues, with the terminal repeat function of the virus normally residing within the last 100–200 bp of the virus genome remaining undisrupted. Optionally, the CELO virus and CELO virus DNA of the invention may, in addition, have a deletion in the region defined by the open reading for the CELO dUTPase (794–1330).

The CELO nucleotide sequence numbering used in the present invention is derived from reference 6, WO 97/40180 and GenBank U46933, which describe the sequence of the wild type CELO virus genome.

Since CELO AIM46 and its derivatives defined above allow the insertion of large pieces of foreign DNA, they are useful as starting material for producing CELO virus vectors.

It has surprisingly been found that a 3.3 kb insert is tolerated by CELO AIM46 without impairing virus growth, thus it may be expected that larger DNA up to approximately 10 kb inserts may be acceptable for the virus. The maximum size limit can be easily tested by the artisan in routine experiments by gradually increasing the insert size and determining the viral growth parameters, as in the experiments of the present invention.

Apart from allowing the insertion of an expression cassette for genes, the recombinant CELO virus of the invention has been shown to be able to replicate without complementation both in LMH cells and in chicken embryos.

A further advantage of the recombinant CELO virus of the invention is that it yields quantities of virus that are comparable to wild type CELO. Furthermore, it was found that AIM46 vectors transduce mammalian cells comparable to Ad5 vectors, demonstrating efficient mammalian cell receptor binding and/or entry activity by CELO vectors.

Since the CELO AIM46 deletion of 41731–43684 removes only part of the open reading frame beginning at nt 41002, the entire ORF should be dispensable and may therefore be deleted. Thus, the deletion may encompass the sequence from nt 41002–43684.

In an embodiment of the invention, the gene of interest is inserted in other genomic sites than the deleted region from nt 41731–43684, 41523–43684, 41002–43684 or 40065–43684, respectively; in this case the vector provides additional space for insertion of further foreign genetic material. Any region that proves to be dispensible may be chosen, a preferred region for inserting foreign DNA is at the dUTPase open reading frame (nt 794–1330).

The virus of the invention grows to wildtype levels and forms the basis of a replication competent vaccine strain. CELO AIM46 was also used to begin analysis of the cell tropism of CELO in regard to both species and cell types, generating information that is important for developing applications of this vector. CELO AIM46 and its derivatives comprising additional modifications, can be used to deliver genes into avian cells with efficiencies of 10–100 fold better than an Ad5 vector bearing the same marker gene. Surprisingly, in a variety of mammalian cell types, e.g. human, bovine, equine, monkey, murine, canine, CELO AIM46 functions with efficiencies that are comparable to an Ad5 vector demonstrating the utility of CELO vectors for mammalian gene transfer applications.

In a further embodiment, the invention relates to the production of recombinant CELO AIM46 virus and its derivatives.

For production of recombinant CELO virus, the CELO virus DNA is introduced into cells that support CELO virus replication. Any standard method for gene transfer may be used for introducing the DNA, e.g. transfection, microinjection, etc. Preferably, the viral DNA is introduced into the cells by polyethylenimine-mediated transfection, as described by (3).

The cells that support CELO virus replication and are thus useful for CELO virus production, may be selected from immortalized cells like LMH (27) or from primary avian embryonic cells, in particular kidney or liver cells. To identify useful cell lines, cells are tested for infectability and the ability to amplify an inoculum of virus.

Alternatively, the recombinant CELO virus may be produced by introducing CELO virus into chicken embryos, preferably by first transfecting the cells described above with CELO virus DNA and keeping the cells in culture for a period of time to produce a quantity of virus sufficient for injection into, and amplification of, the virus in chicken embryos.

In order to produce recombinant CELO virus, regions that are dispensable for viral replication are first identified. To this end, subfragments of the CELO genome which are large enough (e.g. 1,000–15,000 bp) to facilitate reconstruction into the CELO genome and small enough to possess at least one, preferably 5–10, unique restriction sites, are cloned on a plasmid. The plasmid is manipulated with standard restriction enzyme digestion to delete various fragments of the CELO genome and to insert a reporter gene construct in place thereof. This manipulated fragment is then inserted into the full CELO genome, e.g. in a bacterial plasmid, replacing the corresponding wild type fragment using standard ligation or recombination methods. The modified CELO genome is then released from the plasmid backbone by restriction digest and introduced into cells that support CELO virus replication, as exemplified in FIG. 1.

In the case of CELO AIM46 the subfragment contains CELO sequences from nt 1–5503 and 30502–30644 and 40064–43804. An EcoRV fragment from 41731–43684 is deleted and replaced with an expression cassette, e.g. a luciferase expression cassette, to generate pAIM44. This is linearized with HpaI, recombined with wild type CELO DNA to generate pAIM46. CELO sequences are excised from the plasmid by SpeI digestion and introduced into LMH cells to initiate virus replication.

Alternatively, recombination can be performed in avian cells that support viral replication, e.g. LMH cells, by introducing a modified CELO subfragment that contains a deletion/insertion with a second CELO fragment such that overlapping homology between the two fragments allows recombination to full length CELO genome bearing the desired deletion/insertion.

In the experiments of the present invention, the CELO genome regions that are essential for virus replication were identified. Most importantly, a region in the left end of the virus genome that can be deleted and supplied in trans has been identified. This region may therefore be useful for establishing a complementing cell line. Furthermore, a region in the right end of the genome has been identified that can be deleted with no detectable effects on virus replication in either cell culture or in embryos. It has been shown that an expression cassette for foreign genes can be inserted in this region. It has been demonstrated that CELO vectors can package an additional 3.2 kb of DNA sequence over the wildtype genome size, which is already 8 kb larger than Ad5 vectors. Replication competent CELO vectors bearing either a luciferase expression unit or an EGFP expression unit were developed. These vectors were monitored for their ability to transduce a variety of avian and mammalian cell types. As expected, the CELO vectors work much better than an Ad5 vector in avian cells. However, in all mammalian cell types tested, the CELO vectors surprisingly functioned with transduction efficiencies comparable to Ad5 vectors.

The vectors of the invention have vaccine applications in avian species where viral replication can promote immune responses. The ability to propagate the virus in inexpensive chicken embryos facilitates production of large quantities of the vector for any of these applications.

For vaccine applications, the foreign DNA encodes one or more antigens eliciting an immune response in the individual. The antigen may be the natural protein derived from the pathogen, or an immunogenic fragment thereof, e.g. an immunogenic peptide.

To drive expression of the foreign DNA, an expression cassette can be used, which typically includes a promoter active in the target cells, the cDNA of interest, a polyadenylation signal and optionally an intron. Alternately, the DNA inserted into the modified CELO genome may include endogenous CELO promoters, introns and polyadenylation signals to drive expression of the cDNA of interest.

An example for a useful expression cassette, which can be prepared by conventional methods, is the construct described in Example 12 of the present invention, which is derived from a plasmid designated pPM7. It contains the Cytomegalovirus (CMV) immediate early enhancer/promoter followed by a short polylinker with PacI, HpaI and KpnI sites, followed by a rabbit βglobin intron/polyadenylation signal. The CMV/β-globin material may be derived from plasmids available in the art (e.g. from the plasmid pLuc (74), which carries the luciferase gene), modified by PCR to add flanking restriction sites, e.g. BamHI, and subsequently modified by homologous recombination to replace the luciferase cDNA with a PacI/HpaI/KpnI polylinker. The final BamHI cassette can be cloned into pSP65 to generate pPM7. cDNAs to be cloned into CELO AIM46 derivatives are first cloned into pPM7 using the unique restriction sites (PacI/HpaI/KpnI). Subsequently restriction or PCR fragment, e.g. a BamHI fragment, is prepared containing the CMV promoter/cDNA/β-globin unit which is introduced into PacI linearized pAIM46 by homologous recombination. The CMV and βglobin sequences provide homology for the recombination and the luciferase cDNA is thus replaced with the novel cDNA of interest.

The expression cassettes described above can be modified, e.g. by using, instead of the CMV enhancer/promoter, a variety of other viral or cellular promoters including, but not limited to the SV40 enhancer promoter, the Rous Sarcoma Virus long terminal repeat (RSV LTR), the human β-actin promoter, the CELO virus major late promoter, the adenovirus major late promoter, the rat insulin promoter.

Alternatives to to the rabbit β-globins intron/polyadenylation signal include, but are not limited to the intron/polyadenylation signals from SV40, introns and polyadenylation signals from other viruses and from cellular genes could also be used.

Alternately to using an expression cassette, the foreign cDNA may be a simple insert within a region defining CELO AIM 46 or the deoxyUTPase, thus using endogenous CELO regulatory sequences, e.g promotor, intron, polyadenylation signal.

In the case that two different foreign cDNAs are to be expressed from the CELO vector, e.g. cDNAs encoding two different antigens from a pathogen, the following strategies may be used: in a first embodiment, two gene expression cassettes (carrying different cDNAs and different regulatory sequences) can be inserted into the CELO genome. Alternately, an internal ribosome entry site (IRES) can be used to provide expression from two cDNAs using a single promoter, as described by e.g. 70; 67; 71; 72. Thus, a typical expression cassette for CELO AIM46 carrying two cDNAs to be expressed, includes a promoter, the first cDNA, an IRES, and the second cDNA followed by an optional intron and by a polyadenylation signal.

The foreign cDNA, e.g. antigen cDNA, can be isolated from the genomes of the pathogens by standard methods, e.g. by PCR or by restriction digest, optionally including reverse transcription to convert RNA to DNA, and introduced into a transfer vector carrying the regulatory sequences and unique restriction sites, e.g. the pPM7. Subsequently, this antigen expression unit is recombined into a linearized plasmid bearing the CELO genome and having the same regulatory sequences and corresponding restriction sites, e.g the plasmid pAIM46. The resulting CELO-AIM46 vector, carrying the antigen cDNA, can be grown and purified from chicken embryos.

Examples for antigens useful for vaccine applications are given in WO 97/40180, which is fully incorporated by reference herewith.

Further examples for antigens that may be carried by the virus for vaccination applications are antigens of the infectious bursal disease virus (IBDV; 64) and antigens of Chicken coccidia, e.g. *Eimeria acervulina, Eimeria brunetti, Eimeria maxima, Eimeria mitis, Eimeria necatrix, Eimeria praecox* and *Eimeria tenella* (61, 62, 63), examples for antigens are a parasite refractile body transhydrogenase, lactate dehydrogenase, Ea1A and EaSC2 (reviewed in 77).

Further examples for antigens are the glycoprotein C (gC, glycoprotein gIII) of the porcine pathogen pseudorabies virus (the causative agent of Aujeszky's disease (75; 76; 69). A CELO AIM46 vector carrying gC can be used to elicit an anti-pseudorabies response in pigs.

As mentioned above, a robust immune response is to be expected from a replication competent virus. Therefore, a vector is most useful in a host where replication is partially or fully permissive. In this regard, the CELO vectors of the present invention, CELO AIM46 and its derivatives, are ideally suited for avian vaccine applications.

The recombinant CELO virus vectors of the invention are also useful in human vaccine applications, in this case, the foreign DNA encodes an antigen derived from a human pathogen.

CELO vectors based on the CELO genome modified according to the present invention are also useful for gene transfer applications in mammalian systems; an additional argument for pursuing a non-human adenovirus coming from the experience with human adenovirus in human gene therapy applications. Pre-existing immune responses to human adenovirus can impair the initial transduction by human adenovirus based vectors or might exacerbate the cellular immune response to transduced cells. A patient may have no immune experience with an adenovirus from a distant species (although 2 of 7 patients had neutralizing antibodies to the canine adenovirus vector; 30) and initial transductions will not be compromised by the host response to viral antigens. Except for certain agricultural workers, a previous immune exposure to CELO antigens would not be expected in most of the human population. CELO vectors might therefore have an advantage over vectors based on more common human adenovirus serotypes.

An additional conceptual advantage of CELO based vectors of the invention is that CELO, like the bovine, ovine, and canine adenoviruses, is naturally replication defective in human cells. Thus, replication of these vectors will not occur in human patients even in the presence of a wildtype human adenovirus infection.

Furthermore, the ability to generate a replication defective CELO vector will be facilitated by the deletion analysis performed in the present invention. The findings of the present invention provide the basis for constructing cell lines expressing CELO complementing functions.

For gene therapy applications, the foreign DNA may comprise any one or more DNA molecules encoding a therapeutically active protein. Examples are immunomodulatory proteins like cytokines; receptors, enzymes, proteins effecting apoptosis, proteins modulating angiogenesis, e.g. sFLT, FGF receptors, etc. For tumor vaccine applications, the foreign DNA encodes one or more tumor antigens or fragments thereof, preferably in combination with a cytokine.

Examples for human vaccine applications, gene therapy and tumor vaccine applications are given in WO 97/40180, which is fully incorporated by reference herewith.

For vaccine applications, the vector of the invention may be packaged as an enteric coated dosage unit, or in an injectable form for intramuscular, intraperitoneal or subcutaneous injection. Alternately, the vector may be admistered as a paste or a fluid intranasally or intratracheally, as an aerosol or as an intraocular drop. The vector may also be supplied incorporated in feed pellets or in the drinking water.

The quantity of virus introduced per patient, animal or egg may range from 1 to $10^{12}$ particles.

The virus preparation may include a physiological buffered saline or HEPES buffered saline and may optionally mixed with adjuvants such as vitamin-E acetate, oil/water emulsion, aluminium hydroxide, -phosphate or -oxide, mineral oil emulsions such as Bayol$^{(R)}$ or Marcol 52$^{(R)}$ and saponins.

It may be useful to use a freeze-dried form of the virus as a vaccine (78). The inclusion of a stabilizer such as 10% sucrose may be used with a controlled two-step drying process(78). Alternative stabilizers include carbohydrates such as sorbitol, mannitol, trehalose, starch, sucrose, dextran or glucose, proteins such as albumin or casein, or their degradation products.

In vaccine applications, in order to enhance the host immune response, the immune response elicited by the application of the CELO vaccine vector that carries a specific antigen, can be boosted by additionally adminstering the same antigen or an immunogenic fragment thereof. Preferably, the additionally administered antigen is recombinant; it can be obtained by standard methods or by the method described below that uses CELO vectors to obtain the recombinant proteins from eggs. The combined application of the vector and the antigen can be performed as described by (65, 73). Preferably, the recombinant antigen is administered, optionally together with an immunostimulating adjuvant, subsequent to the CELO vector.

In a further aspect of the invention, CELO virus is used for producing any protein of interest.

In this embodiment of the invention, the CELO virus, e.g. CELO AIM46 or its derivatives, is engineered, as described above, by introducing the cDNA or, preferably, an expression cassette, encoding the protein of interest into one of the insertion sites of the recombinant CELO DNA of the invention. Virus may be obtained by replication in suitable cells, as described above, and the recombinant virus is introduced, preferably by injection into the allantoic cavity of an avian embryo. Preferably, approximately $4 \times 10^7$ particles are introduced into the allantoic cavity of 7 to 9 day old chicken embryos, which are subsequently incubated for three to four days at 37° C. The recombinant material is then recovered from the allantoic fluid, serum, yolk, amniotic fluid or from the embryo itself.

The protein of interest may be an intracellular or a secreted protein. In the case of a intracellular protein, which is exemplified by the reporter protein eGFP in the experiments of the present invention (Example 11), the protein can be recovered by lysing infected cells that accumulate in the allantoic fluid. In the case of a secreted protein, the material can be recovered from various extracellular fluids of the embryo (allantoic fluid, amniotic fluid, serum, yolk) or, in analogy to the recovery of intracellular proteins, by lysing infected cells.

In a preferred embodiment, the protein of interest is expressed as a fusion protein comprising the protein and, as a stabilizing sequence, an immunoglobulin Fc domain. The secretion of the recombinant protein can be directed by the natural signal sequence from the protein, which may, in addition to the signalling function, have a stabilizing function. The Fc domain confers stability to the protein in the extracellular space and provides a protein sequence that can be used for affinity purification of the recombinant protein using, for example, Protein A or Protein A/G chromatography resins. Constructs that include an Fc domain for stabilization and are thus useful to be expressed from CELO, have been employed to make soluble forms of the FGF receptor 2 (sFGFr; 66) and the VEGF receptor 1 (sFLT; 68).

As alternatives to the signal sequences of FLT and the FGF receptor, signal sequences from or fusions with the proteins ovalbumin, conalbumin, avidin and lysozyme can be used. These are proteins that are synthesized in the liver and/or oviduct of chickens and accumulate within the egg. Thus, using part or all of the coding sequence of these proteins fused to a protein of interest are expected to yield secreted recombinant proteins that are stable within the developing embryo; furthermore, using sequences of this type, e.g. avidin, provides a tag that facilitates chromatographic purification

BRIEF DESCRIPTION OF THE FIGURES

FIG. 1A shows construction of a plasmid bearing the termini of the CELO genome (panel A) and cloning of full length CELO genome as a bacterial plasmid (panel B). FIG.

1B shows cloning of modified versions of the CELO genome (panel C).

Figure 2:
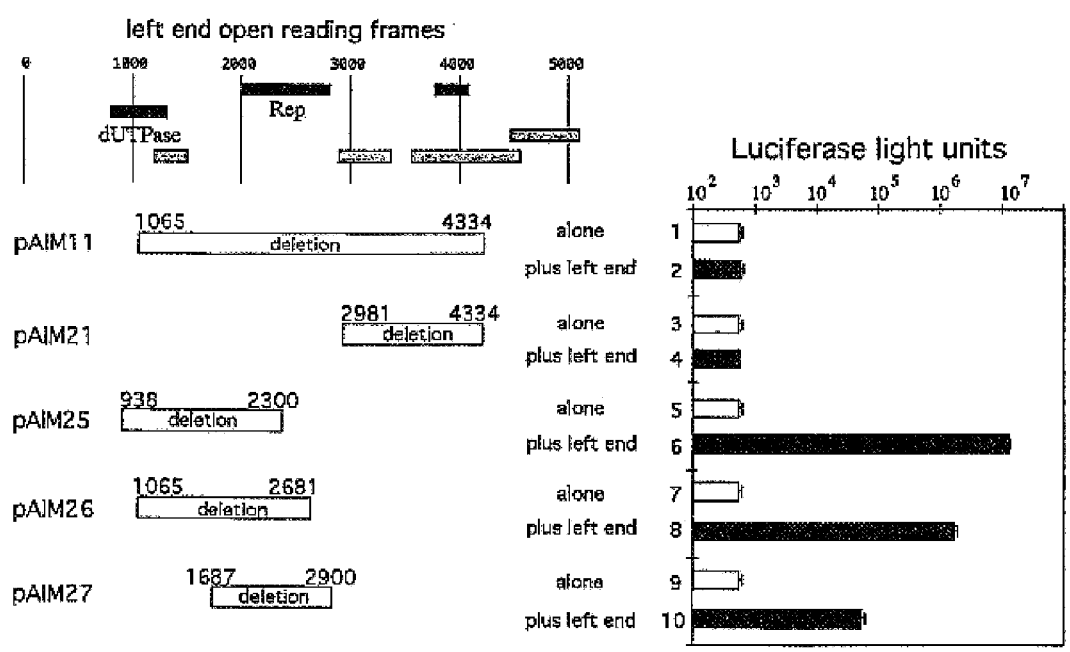

FIG. 2. Analysis of CELO left end mutations FIG. 2, upper panel: Open reading frames FIG. 2, lower panel: Analysis of replication FIG. 3. Analysis of CELO right end mutations FIG. 3, upper panel: Open reading frames FIG. 3, lower panel: Analysis of replication FIG. 4. PCR analysis of wt CELO vs. CELO AIM46

FIG. 5. Immunofluorescence, monitoring the replication of wildtype CELO vs. CELO AIM46

FIG. 6. Heat stability of AIM46 vs. AdLuc

Figure 7:
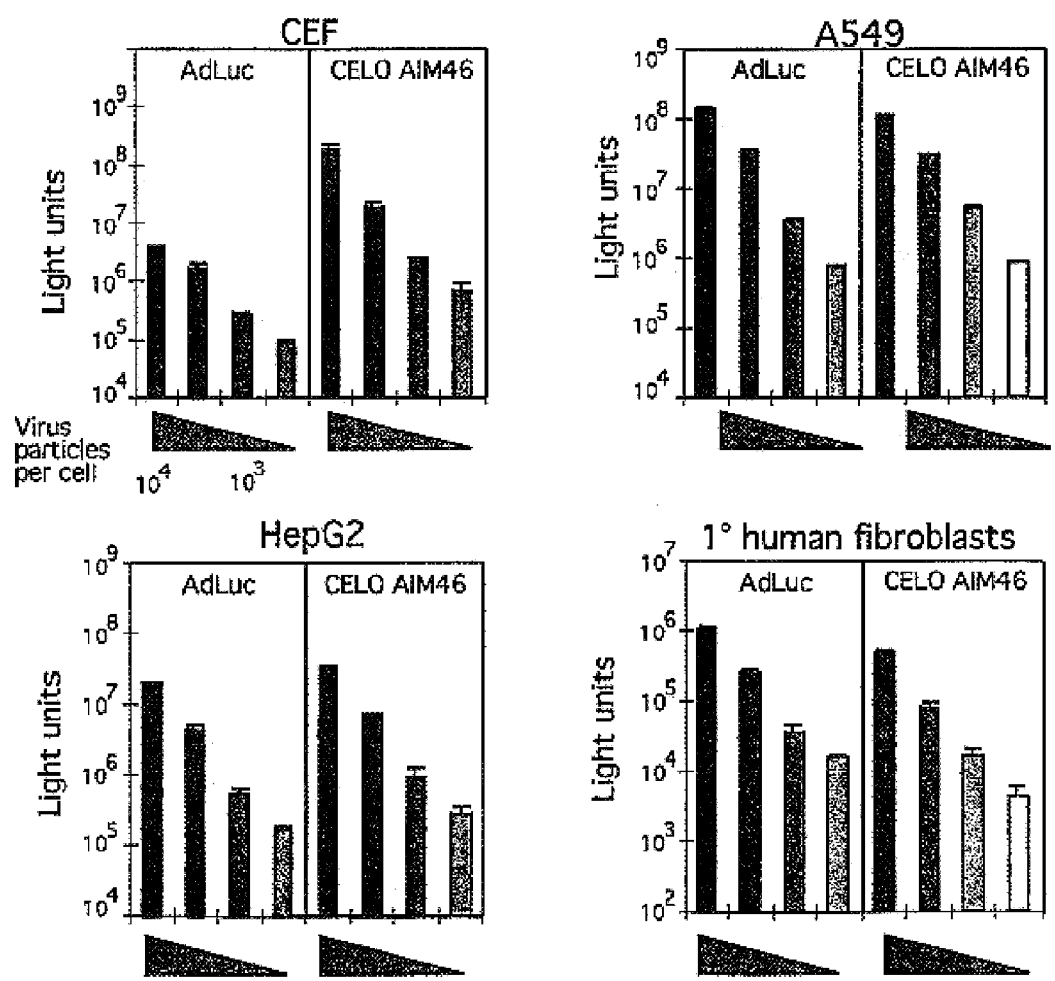

FIG. 7. Tropism of CELO vs. Ad5

Figure 8:
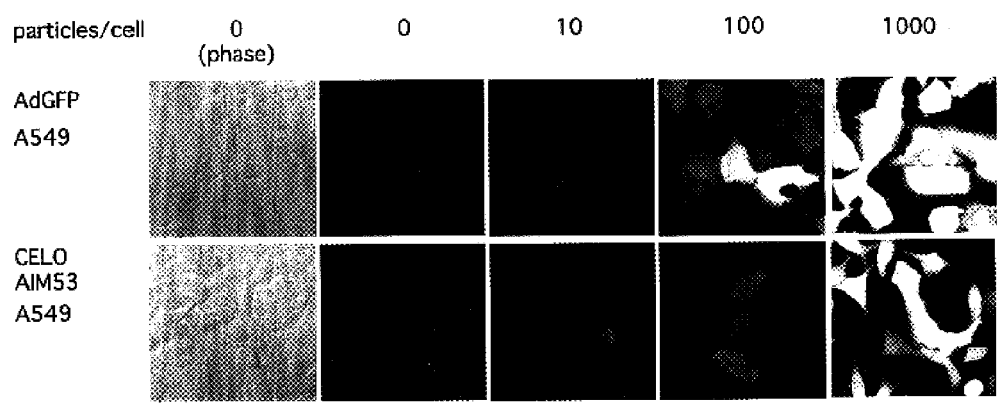

FIG. 8. Transduction of EGFP using recombinant Ad5 or CELO vectors

Figure 9:
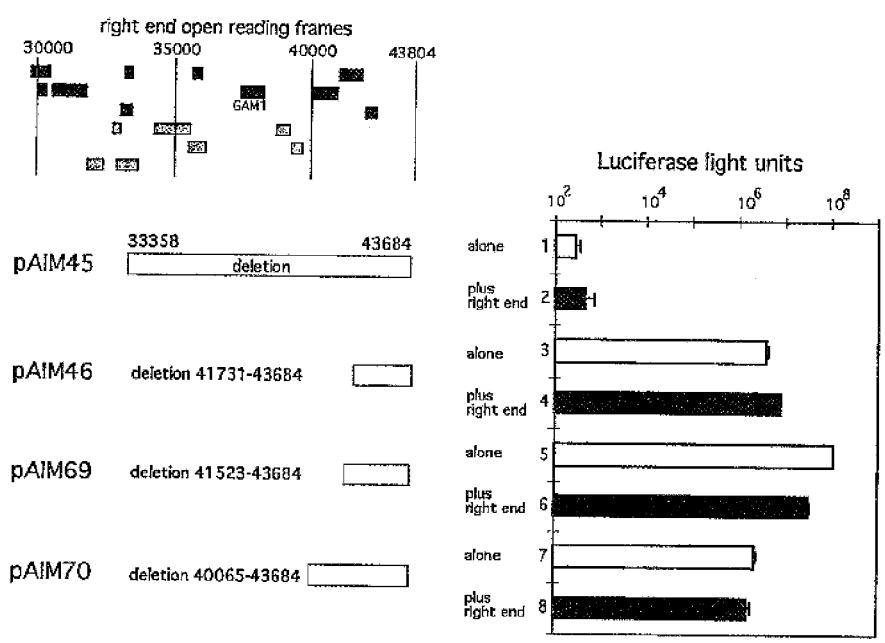
Figure 10A:
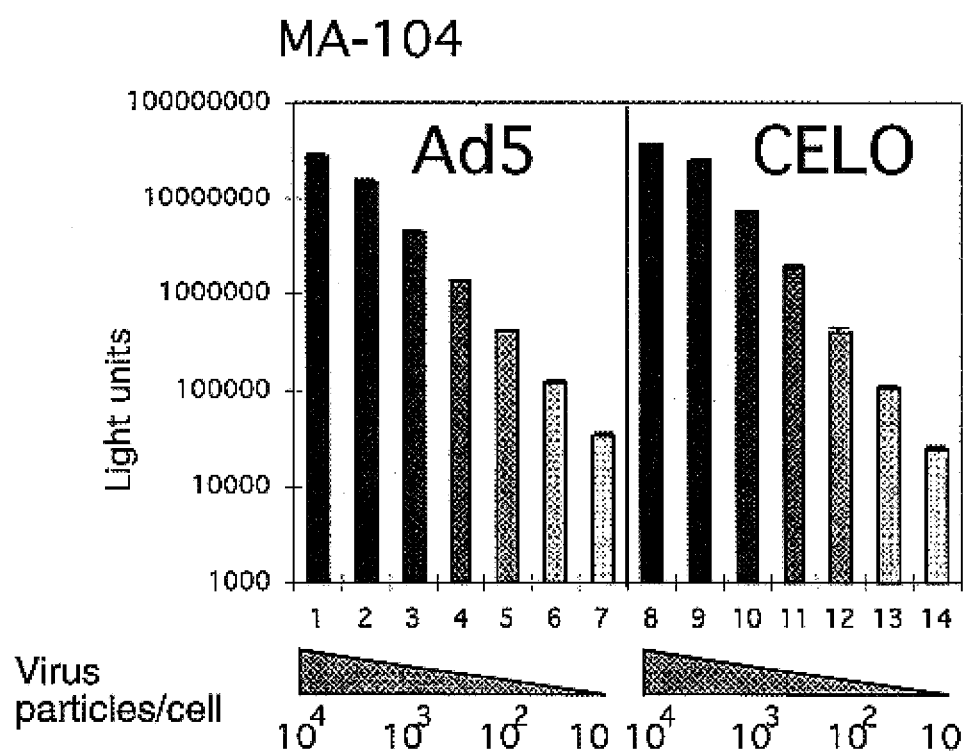
Figure 10B:
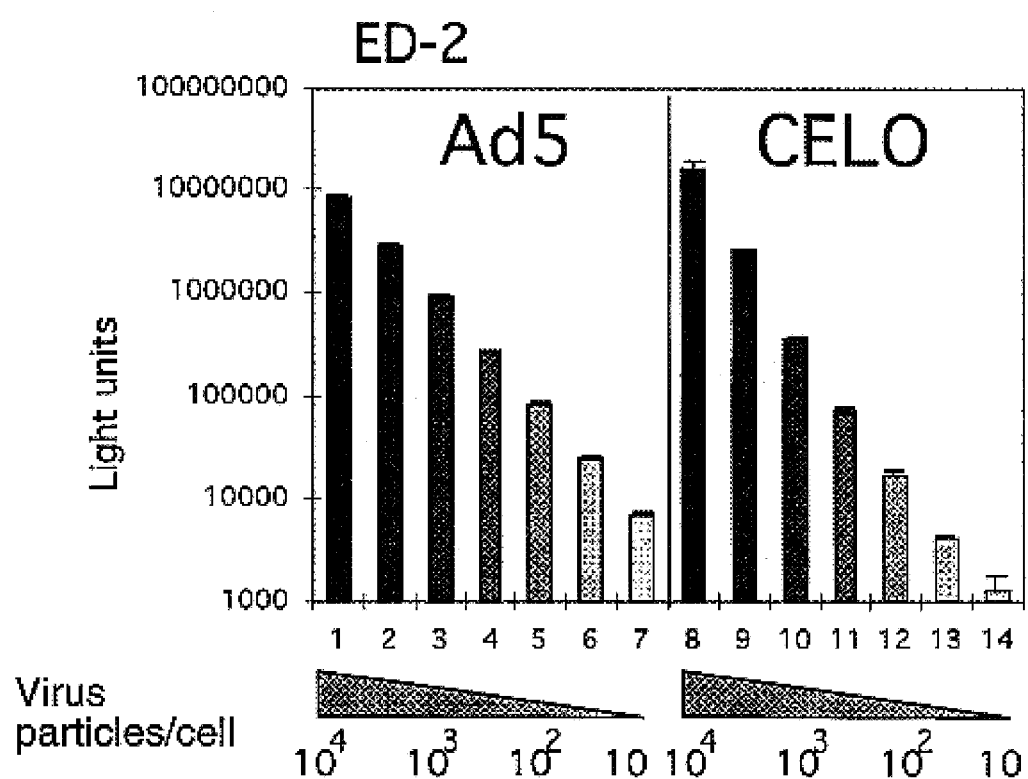
Figure 10C:
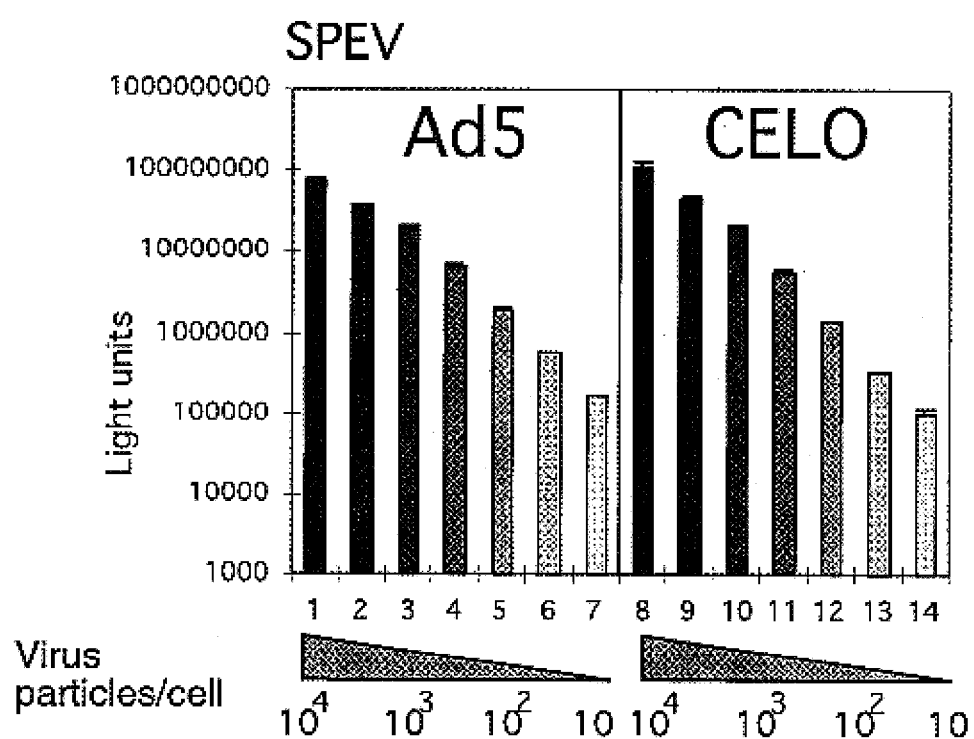
Figure 10D:
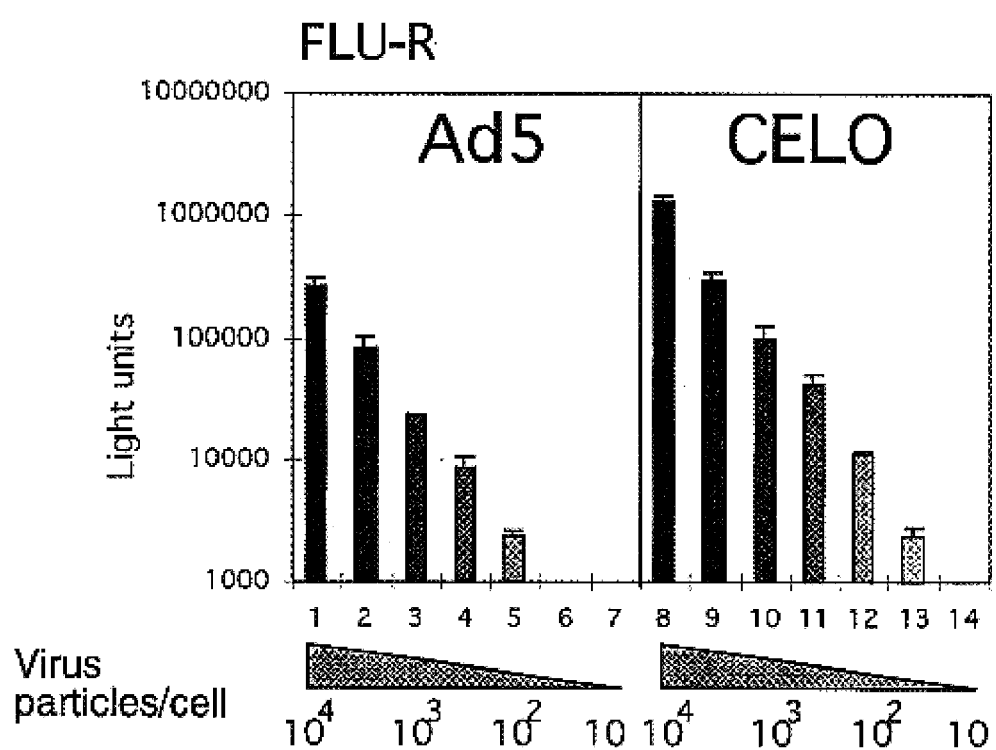
Figure 10E:
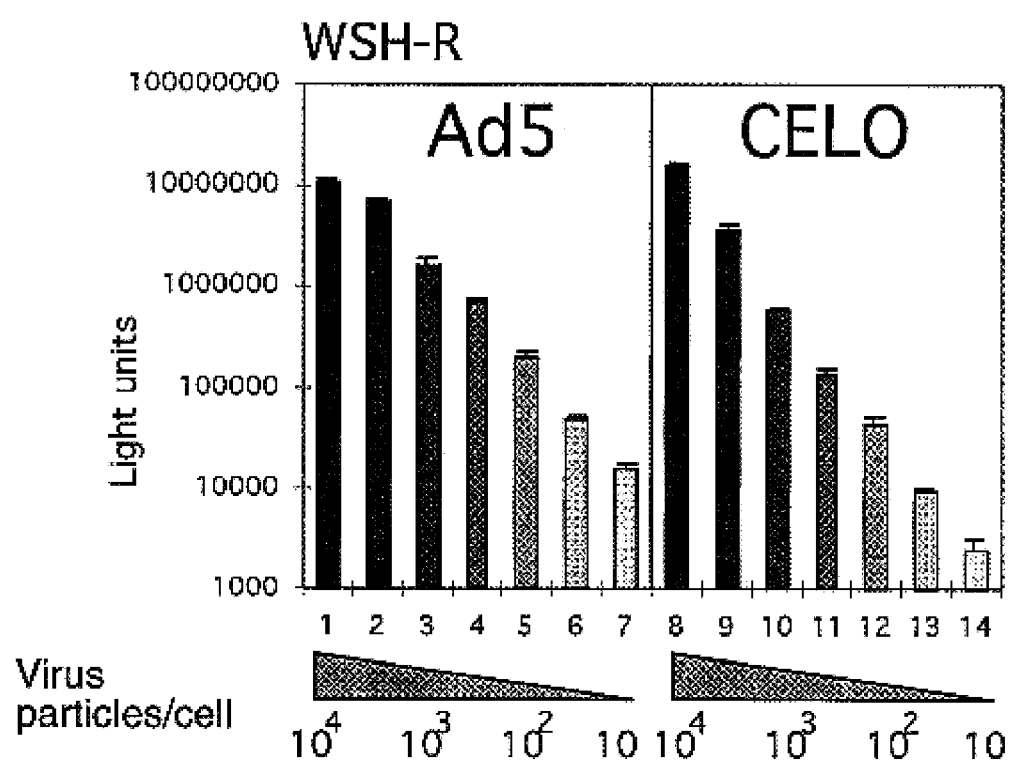
Figure 10F:
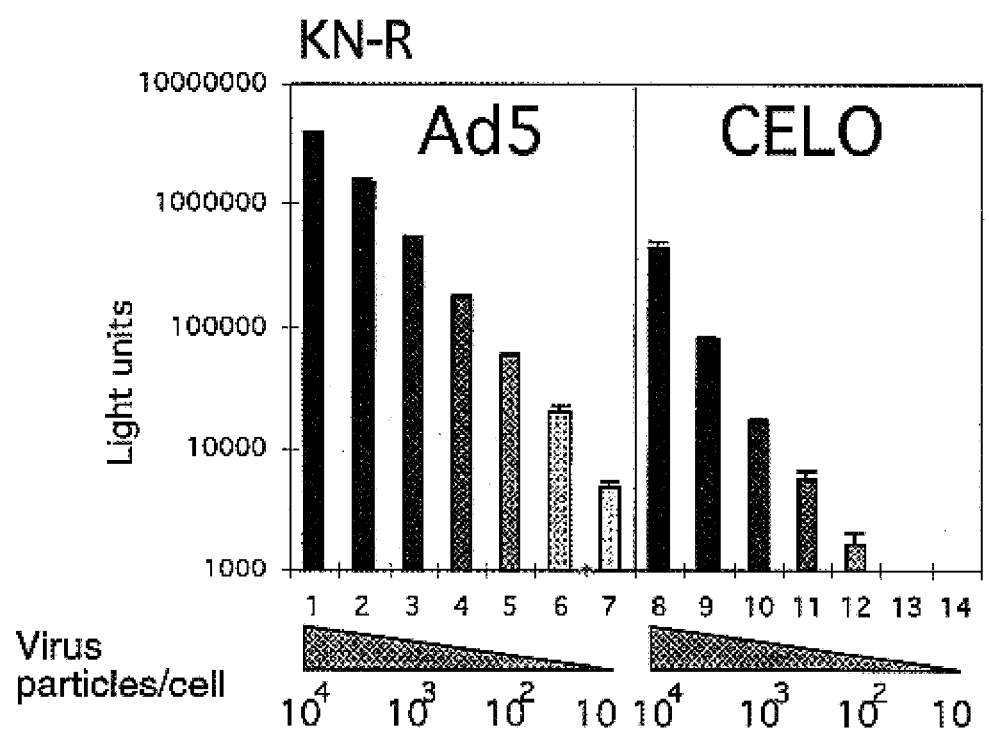
Figure 10G:
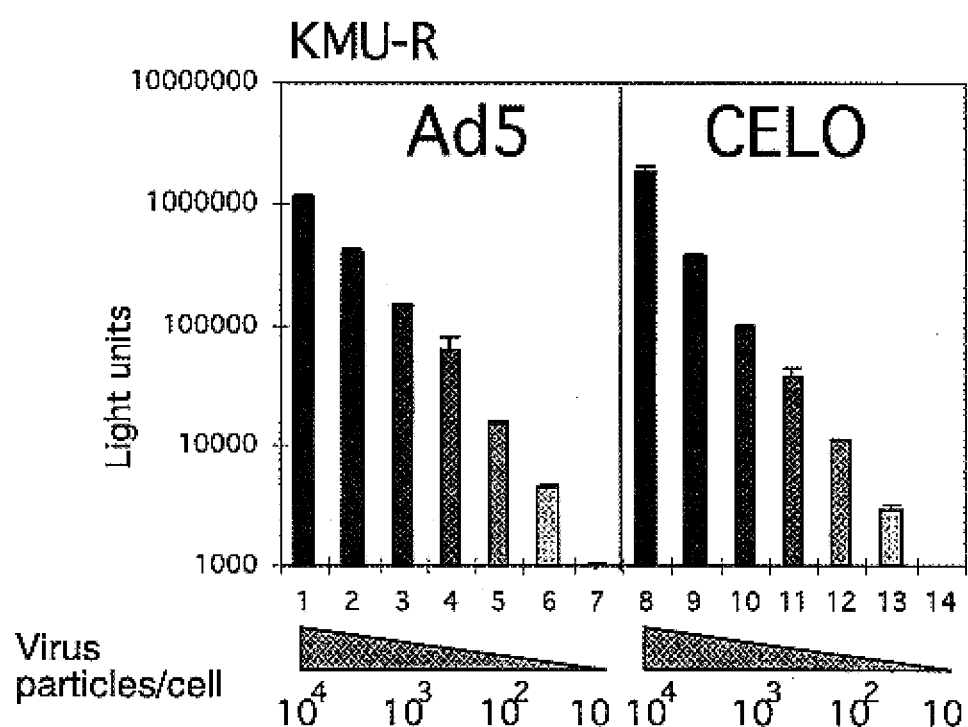
Figure 10H:
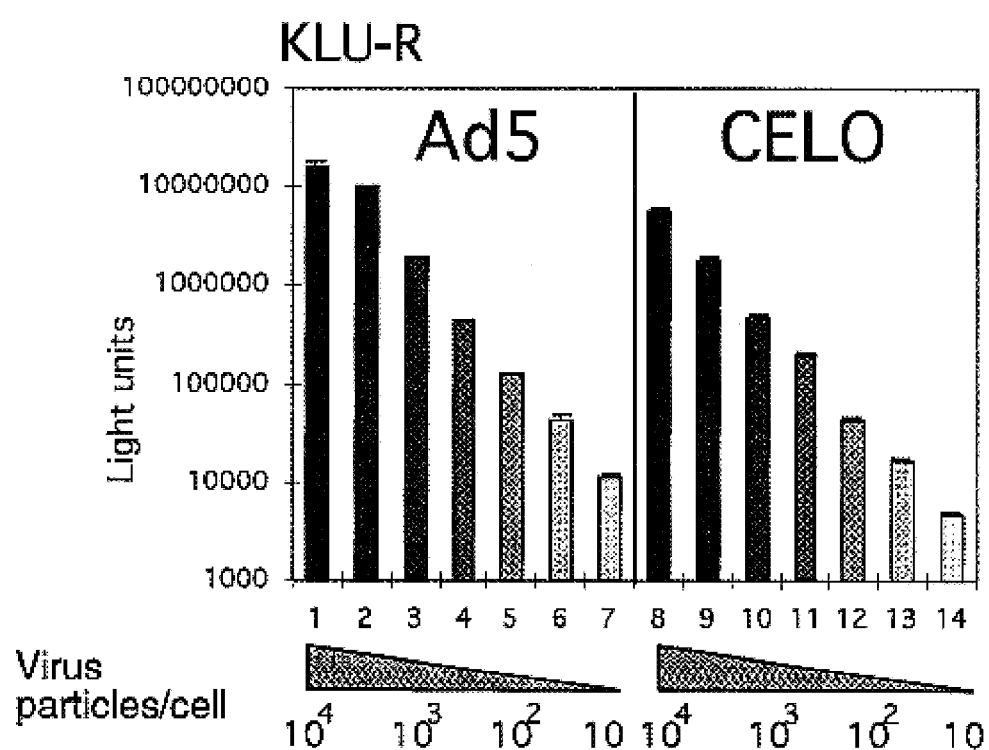

FIG. 9. Analysis of CELO right end mutations FIG. 9, upper panel: Open reading frames FIG. 9, lower panel: Analysis of replication FIG. 10. Tropism of CELO AIM46 for different animal species FIG. 11. Production of recombinant GFP by a CELO AIM46 derivative FIG. 12. Production of soluble Fc-stabilized recombinant protein by a CELO AIM46 derivative Unless otherwise stated, the following materials and methods were used in the Examples:

a) Cloning the Terminal Fragments of the CELO Genome

The two terminal HindIII fragments of CELO were cloned. CELO genomic DNA (CsCl purified) was digested with HindIII, the 1601 bp left end fragment and the 959 bp right end fragment were purified from a low melting agarose gel. The 5' ends of adenovirus genomes are linked by a phosphodiester bond to a serine residue on the viral terminal protein (22, 47). The peptide remaining after proteinase digestion must be removed to allow ligation and cloning. Accordingly, the terminal peptides were removed from the DNA fragments by adding NaOH to 0.3 N and heating at 37° C. for 90 minutes (22). The solutions were then cooled to room temperature, Tris pH 7.4 was added to 0.1 M and HCl was added to 0.3 M to neutralize the NaOH. The fragments were heated to 56° C. for 20 minutes and slowly cooled to room temperature (1 hour) to facilitate reannealing. The DNA was then purified (Qiaquick column, Qiagen), SpeI linkers (New England Biolabs cat #1085) were added and each fragment was cloned via SpeI and HindIII sites into a pBR327 (GenBank L08856, ref. 51) derivative containing an SpeI site in a destroyed EcoRI site (see FIG. 1A). Both the left and the right terminal HindIII fragment were cloned in this manner and DNA sequence analysis was performed to verify both terminal 300 bp of both fragments.

Subsequently, the two CELO end fragments were cloned into a pBR327 derivative containing an SpeI site, a destroyed EcoRI site and a ClaI/BamHI excision to remove the second Hind III site, creating the plasmid pWü-H35 (see FIG. 1A).

b) Cloning the Entire CELO Genome

HindIII-linearized, alkaline phosphatase treated pWü-H35 vector was mixed with purified CELO virus DNA and introduced into electrocompetent *E. coli* JC8679 (17, 42) by electroporation. Recombination between the CELO terminal sequences on pWü-H35 and the termini of the CELO genomic DNA generated an plasmid containing a full length CELO genome (pCELO) flanked by SpeI sites (FIG. 1B).

c) Modifications in the Left End of the CELO Genome

The luciferase cassette containing the Cytomegalovirus immediate early enhancer/promoter, the luciferase cDNA (14) followed by a rabbit βglobin intron/polyadenylation signal was derived from pCLuc (45), modified by PCR to add flanking BamH1 sites and cloned into pBlueScript II (SK) to generate pBlueLuc. For most of the CELO insertions, the luciferase cassette was isolated from pBlueLuc by BamH1 digestion and the termini were made blunt by treatment with Klenow enzyme.

Modification of the left end CELO region were made using pAIM3, which contains, on a pBR327 backbone, the CELO left end (nt 1 to 5501) and a portion of the right end (nt 30500 to 30639 and nt 40065 to 43804; derived by removing an Asp718 fragment from pWüHpa). The deletions in the CELO genome involved digestion of pAIM3 at two enzyme sites in the CELO left end sequence, excision of the sub-region followed by insertion of a luciferase cassette. All manipulations were confirmed by restriction analysis and sequence analysis. This strategy was used to generate the transfer plasmids pAIM7, 16, 22, 23 and 24 (see Table 1). The CELO nucleotide sequence numbering is derived from reference 6 and GenBank U46933.

d) Generation of Recombinant CELO Genomes

Figure 1:
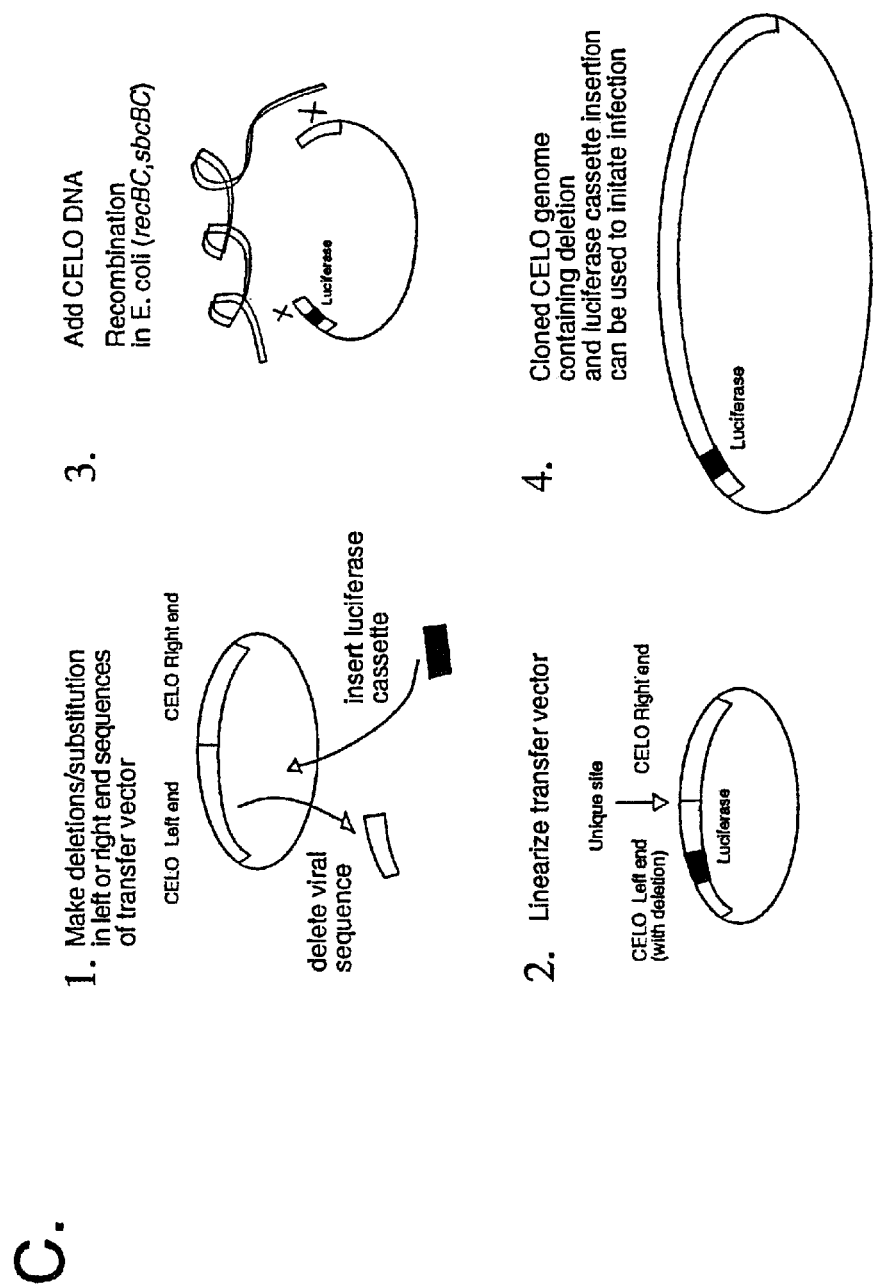
FIGS. 1A and 1B show construction of plasmids carrying wildtype and mutant CELO genomes.

The plasmids pAIM7, 16, 22, 23 and 24 were linearized by double digestion using Asp718 and HpaI, and recombined with purified CELO DNA using homologous recombination in *E coli* BJ5183 (5, 13) to generate the CELO genome plasmids pAIM11, 21, 25, 26 and 27. FIG. 1C and Table 1 illustrate the applied technique:

FIG. 1C shows the cloning of modified versions of the CELO genome. Step 1: Transfer vectors were produced by manipulating subfragments of the CELO genome, as either pWü-H35 (with the terminal HindIII fragments of CELO) or pWüHpa (with the terminal Hpa I fragments of CELO) using standard ligation cloning methods in order to delete portions of the CELO genome and insert a luciferase cassette. Step 2: the linearized transfer vector was recombined with wildtype genomic CELO DNA. Recombination occurs in two ways, either to include the deletion/luciferase cassette or to exclude the deletion/luciferase cassette to generate a wildtype CELO plasmid. Plasmids bearing the desired mutation were identified by restriction enzyme digestions and sequencing and used to initiate virus infection.(all constructs were sequenced across the deleted regions to verify the construct; see Table 1).

e) Modifications in the Right End of the CELO Genome

Using methods similar to those described above, plasmids containing both the left and right HpaI fragments of CELO were generated and manipulated to insert the luciferase cassette and to remove an EcoRV fragment from either 33358–43684 (pAIM43) or 41731–43684 (pAIM44). These plasmids were linearized at the unique Hpa I site and recombined in BJ5183 cells with wildtype CELO DNA to generate either pAIM45 or pAIM46.

f) Evaluation of the Recombinant CELO Genomes on LMH Cells and Preparation of Viral Stocks The recombinant CELO plasmids were digested with SpeI to release the viral genome from the plasmid, extracted with phenol, with chloroform and then purified by gel filtration (Pharmacia Nick Column) equilibrated with TE.

Transfection complexes were prepared using a modification of the PEI technique (1, 3). The DNA was condensed with PEI in two steps as follows: PEI MW 2000 (2.5 µl of 10 mM PEI in 125 µl HBS (150 mM NaCl, 20 mM HEPES, pH 7.4)) was added dropwise to 3 µg of DNA diluted in 125 µl of HBS. The sample was incubated at room temperature for 20 minutes. Subsequently, PEI MW 25000 (3.5 µl of 10 mM in 125 µl of HBS) was added dropwise to the sample and the complex incubated at room temperature for an additional 20 minutes. Leghorn Male Hepatoma (LMH) cells (27) were seeded the day before transfection in 24 wells plates at 7×10⁴ cells/well (24 well dish). For transfection, the cell culture medium was replaced by 400 µl DMEM supplemented with 10 µg/ml polymyxin B (no serum). The transfection complex (90 µl per well) was added to the cells for 4 hours at 37° C. after which the medium was replaced with fresh, serum containing medium. Transfection effiency was monitored by measuring luciferase activity in cell lysates at 24 hours post-transfection.

To test for amplification of virus, cleared lysates from transfected or transduced cells were prepared as follows. Cells plus supernatant were harvested, collected by centrifugation and the cell pellets were resuspended in 2 ml of processed supernatant. The material was frozen and thawed 3 times, sonicated in a bath sonicator to release viral particles, the cell debris was removed by centrifugation, and the cleared lysate used for further amplification on fresh cultures of LMH cells. CELO purification by CsCl gradient was performed as previously described (9). Virus was quantified based on protein content with the conversion factor of 1 mg/ml protein equal to $3.4 \times 10^{12}$ virus particles/ml (34).

g) Construction of a EGFP Expressing CELO AIM 46 Derivative (CELO AIM53)

The luciferase cDNA in pAIM46 was replaced by an EGFP cDNA to generate pAIM53. The replacement was obtained by homologous recombination in *E coli* between pAIM46 linearized at the unique PacI site in the luciferase cDNA, and pAIM52, a transfer plasmid carrying an EGFP cDNA under the control of the same CMV promoter and β-globin intron and polyadenylation signal used in the luciferase cassette of pAIM46, thus providing homologies for recombination.

h) Construction of pPM7

The transfer plasmid pPM7 contains the Cytomegalovirus immediate early enhancer/promoter followed by a short polylinker with PacI, HpaI and KpnI sites, followed by a rabbit β-globin intron/polyadenylation signal. It was obtained as follows: The CMV/β-globin material was derived from pCLuc (74), modified by PCR to add flanking BamH1 and modified by homologous recombination to replace the luciferase cDNA with a PacI/HpaI/KpnI polylinker. The final BamHi cassette was cloned into pSP65 to generate pPM7.

j) Generation of Recombinant type 5 Adenoviruses

AdLuc: The luciferase cassette was cloned via the flanking BamHI sites into pDE1sp1B (2), to produce pDE1sp1BLuc, with the luciferase cDNA in the same orientation as E1 transcription. Recombinant virus was generated using recombination after cotransfecting pDE1sp1BLuc with pJM17 (2) into 293 cells (19). 10 days post transfection, cells lysates were prepared, used to infect fresh 293 monolayer and virus was amplified from a single plaque. The virus stock used here was prepared from material that was subsequently passed through 2 additional rounds of plaque purification, amplified, purifed by banding in CsCl and quantified by protein content (1 mg/ml protein= $3.4 \times 10^{12}$ virus particles/ml; ref. 34). AdGFP: A fragment containing the CMV promoter, EGFP coding region and SV40 poly A sequences was excised from the pEGFP-C1 (Clontech) using Ase1/Mlu1. Overhanging ends were filled in by Klenow and cloned into the EcoRV site of pDE1sp1B (2) with the EGFP cassette in the same orientation as E1 transcription. Recombinant virus was generated as described above using recombination with pJM17 in 293 cells.

k) Analysis of Heat Stability of Viruses

CELO AIM46 and AdLuc were diluted to $4 \times 10^9$ particles/100 µl concentration in HBS (final glycerol concentration was 2.4% (vol/vol.) and exposed for 30 minutes to temperatures ranging from 48 to 68° C. Subsequently, aliquots of the virus were tested for the ability to transduce luciferase activity into either A549 or CEF38 cells.

1) Immunofluorescence

LMH cells were plated on gelatin-coated glass slides (Labtek, Nunc) at $10^5$ cells/chamber and infected the next day with CELO AIM46 or wilde type CELO virus at 500 viral particles/cell in DMEM medium containing 2% FCS. At the indicated time points after the infection, cells were fixed in cold methanol:acetone (1:1) at room temperature and CELO proteins were visualized by immunofluorescence as follows: nonspecific binding sites were blocked using PBS+1% BSA at room temperature for 1 hr. Polyclonal anti-CELO antibody was diluted 1:1000 in PBS+1% BSA and incubated for 1 hr. After three, 5 minute washes in PBS at room temperature, a goat-anti-rabbit (Boehringer-Mannheim) detection antibody coupled to FITC (1:400 dilution) was added in PBS+1% BSA. The slides were again washed, DAPI was included in the last wash for visualization of the nuclei and the slides mounted in MOWIOL for examination by fluorescence microscopy.

m) Generation of Anti-CELO Virion Polyclonal Serum

Rabbits were injected with 100 µg of CsCl purified, heat inactivated (70° C., 60 minutes) CELO virions in complete Freund's adjuvant, boosted at 2, 4 and 5 weeks with 100 µg of CELO in incomplete Freund's adjuvant and serum was collected subsequently. Western analysis demonstrated that the pooled sera used here reacted specifically with all major CELO capsid proteins but not with lysates of non-infected avian cells.

n) Additional Reagents

Wildtype CELO (FAV-1, Phelps) (Avian adenovirus Type 1, Chicken Embryo Lethal Orphan; CELO American Type Culture Collection: ATCC VR-432; Strain: Phelps; (57)) was purified from infected chicken embryos as previously described (9).

The LMH cell line (27) was obtained from ATCC No. CRL-2117, the A549 cell line was also obtained from the ATCC No. CCL-185, and normal human dermal fibroblasts were obtained from Clonetics and were used between passage 5 and 15. The chicken fibroblast cell line designated CEF38 was established from fibroblasts according to known methods; it allows CELO virus entry but does not support CELO replication. All four cell types were cultured in DMEM/10% FCS.

The 293 cell line (19) was obtained from the ATCC (No. CRL-1573) and was cultured in MEMalpha with 10% newborn calf serum.

The cell line MA-104 (Macaca mulatta (monkey, Rhesus, kidney, embryo, epithelial) was obtained from ATCC (No. CRL-2378).

The cell line ED-2 (equine, dermal fibroblast) was obtained from ATCC (No. CCL-57).

The following cell lines were obtained from BFAfV; Riems (Zellbank für Zellinien in der Veterinärmedizin; BFA f. Viruskrankheiten der Tiere, 17498 Insel Riems):

SPEV (porcine, kidney, embryonal, "verseniert"; catologue No. 8);

FLU-R (porcine, lung, fetal; catalogue No. 113);

WSH-R (wild boar, skin, fetal: catalogue No. 388);

KN-R1 (bovine, kidney, fetal; catalogue No. 028);

KMU-R (bovine, muscle, embryonal; catalogue No. 098);

KLU-R1 (bovine, lung,embryonal; catalogue No. 091).

EXAMPLE 1
Construction of a Plasmid Copy of the CELO Genome

Initially the terminal HindIII fragments of CELO were purified from CELO viral DNA, treated with base to remove the terminal peptides, linkers encoding SpeI restriction sites were added and the two terminal fragments were cloned in the correct orientation into a low copy number plasmid (FIG. 1A depicts the construction of a plasmid bearing the termini of the CELO genome. CELO genomic DNA was digested with HindIII, the two terminal fragments were isolated, treated to remove the terminal peptides and cloned as SpeI, HindIII fragments after addition of SpeI linkers generating the plasmid pWü-H35). This plasmid encoding the two ends of the virus (pWüH-35) was linearized with the unique HindIII site and recombined with CELO genomic DNA to generate a full length CELO genome flanked by SpeI sites on a bacterial plasmid (see FIG. 1B, which shows the cloning of full length CELO genome as a bacterial plasmid. pWü-H35 was linearized with HindIII and recombined with CELO genomic DNA to generate the full length plasmid clones of the CELO genome. The natural terminal repeats were flanked by SpeI sites to allow excision of the viral genome from the bacterial plasmid. There are no SpeI sites within the CELO genome.). Several independent clones of the viral genome were obtained and the correct structure was verified by restriction analysis and by the production of virus upon transfection.

EXAMPLE 2 a) Analysis of Unique Sequences Required for Virus Replication

A screening method for determining the requirement of CELO sequences for virus replication was developed. Deletions were first introduced into bacterial plasmid copies of the viral genome using homologous recombination in bacteria. In all cases the deleted viral sequences were replaced with a luciferase cassette to allow monitoring of both the initial transfection efficiency into cells that support wildtype virus replication and the replication and transduction potential of the mutant virus in subsequent passages. As will be shown below, the CELO genome allows the insertion of at least 1.7 kb of sequence beyond the wildtype genome size, thus the concern that introducing the luciferase cassette itself might impair replication was not realized. The mutant viral genomes were excised from the plasmid and transfected into LMH cells either alone, to determine if the deletion removed essential DNA sequences or with a plasmid bearing the region of the CELO genome that spans the deletion, to determine if complementation of the deletion could occur. Five days after transfection, the cells were lysed, a portion of the lysate was assayed for luciferase activity to monitor transfection efficiency and a second portion was used to infect a fresh monolayer of LMH cells. After another 5 day period, the cells were monitored for cytopathic effect, lysates were prepared and assayed for luciferase and a portion was again used to infect fresh LMH cells.

b) Analysis of CELO Left End

Using the strategy described in a), the unique left end CELO sequences were analyzed for replication function. The map of the left end open reading frames of 99 amino acids and larger is shown in FIG. 2A: Open reading frames of greater than 99 amino acid residue in the left ca. 5000 nt of the CELO genome are indicated in either black (rightward transcription) or grey (leftward transcription). The open reading frames coding for a deoxyUTPase (dUTPase) and a protein with parvovirus REP homologies (REP) are indicated. An open reading frame encoding a functional dUTPase is found at position 784 (54). An open reading frame beginning at position 1991 encodes a protein with significant homology to the parvovirus REP gene. An additional five open reading frames are also indicated.

FIG. 2 shows the analysis of replication. The nucleotide numbers of deletions introduced into the CELO genome are listed in the upper panel of FIG. 2 and in table 2. The modified CELO genomes were linearized with SpeI to release the genome from the bacterial plasmid and transfected into LMH cells either alone, or in the presence of a plasmid (pB5.5) bearing wildtype CELO sequences from 1–5501 ("plus left end"). At 5 days post transfection, cells were harvested, lysed by freeze/thawing and sonication and the lysates were applied to a fresh LMH culture. This amplification was repeated twice and equal aliquots from the third passage of virus were tested for their ability to transduce luciferase activity in LMH cells. The average of three transductions with the standard deviations are indicated.

Mutant genomes were constructed that removed first the entire region (pAIM11) or deleted single or small groups of open reading frames (pAIM21, 25, 26, 27). When introduced into LMH cells by transfection, pAIM11, which has a deletion removing the entire region, was positive for luciferase in the first lysate but unable to transfer luciferase gene expression in subsequent passaging attempts, either in the absence or presence of a complementing left end fragment.

A more discrete mutant (pAIM21) disrupts only three of the unknown ORFs but leaves intact the dUTPase and the REP-like ORFs. However, similar to pAIM11, the pAIM21 genome was also unable to transfer luciferase gene expression in subsequent passaging attempts either in the absence or presence of a complementing left end fragment (FIG. 2B). Thus both of the mutations alter sequences that must be present in cis for virus replication. pAIM27 deletes only REP, while pAIM25 and 26 delete the dUTPase, REP and one unknown open reading frame. These three genomes all produced luciferase activity in the first lysate. Subsequent passage of the material revealed that CELO AIM 25, 26 and 27 were not capable of replicating in the absence of complementation. However, unlike pAIM11 and 21, passageable luciferase activity was observed if the initial transfection contained the complementing left end plasmid (FIG. 2B). These three complemented viruses (CELO AIM25+, 26+ and 27+) were amplified for an additional 6 passages in LMH cells with, surprisingly, only modest declines in their ability to transduce luciferase activity (results not shown). PCR and Southern analysis revealed a substantial contribution of apparently wildtype CELO in the passage 3 material, demonstrating that recombination had occurred that re-introduced the sequences deleted in the original mutants. Thus, an apparently wildtype CELO was produced and provided complementation functions for the luciferase-bearing mutant CELO.

In conclusion, of the left end sequences, a region was identified (between 2981 and 4334) that is essential in cis for virus replication. A second region was identified (between nt 938 and 2900) which is essential for virus replication but could be supplied in trans. Formally, it is possible that a series of recombination events generated a viral genome that contained both the originally deleted sequence and the luciferase cassette, however, the simplest explanation of this pattern is that a simple recombination occured between pB5.5 and the mutant CELO genome to generate a wildtype CELO genome, which in subsequent passages provided complementation activity for a small number of the mutant (luciferase positive) viruses in the mixture. Some of these viral genomes contain net insertions of sequence over the wildtype size with the largest containing a 1616 bp deletion combined with a 3.3 kb luciferase cassette insertion. Thus CELO, which in the wildtype form is already 8 kb larger than Ad5, can package, at least, an additional 1700 bp of sequence.

EXAMPLE 3

A portion of the CELO right end is dispensable

Figure 3:
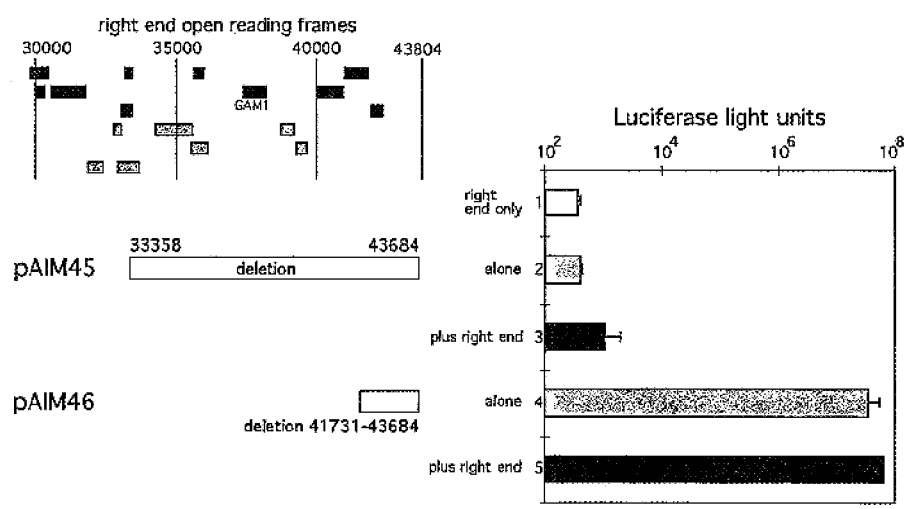

A similar mutational strategy was used for an initial analysis of the right end sequences of CELO. The genome plasmid pAIM45 contains a large deletion from 33358–43684, deleting 10 ORFs of 99 amino acids or larger, including the previously characterized GAM1 gene (FIG. 3, ref. 7). The plasmid pAIM46 contains a more discrete deletion from 41731–43684 and disrupts two ORFs (FIG. 3 depicts the analysis of CELO right end mutations. Analysis was performed as outlined in Example 3, FIG. 2B except that the right end complementing plasmid pB13.3 was used in place of the pB5.5 (lanes labeled "plus right end). Both mutant genomes included a luciferase cassette in place of the deleted sequences.

pAIM45 and pAIM46 were transfected into LMH cells either alone or with a plasmid bearing the wildtype CELO right end sequences (pB13.3). Luciferase activity was obtained in lysates of the transfected cells demonstrating successful transfection (results not shown). Subsequent passage of the material on fresh LMH cells revealed that pAIM45, with the extensive right end deletion, was not capable of generating infectious CELO particles, neither in the absence nor in the presence of the intact right end sequences (FIG. 3). Not surprisingly, this extensive deletion removed sequences that were essential, and most likely some of these are required in cis, as evidenced by the absence of complementation by the wildtype right end sequences. In contrast, pAIM46 genome was found to generate infectious and passageable virus in both the presence or the absence of the complementing genome fragment (FIG. 3). The two disrupted open reading frames in pAIM46 are thus dispensable for cell culture growth of CELO as well as for growth in chicken embryos (see Example 5).

To verify the structure of pAIM46 and of the genome carried by CELO AIM46, a PCR analysis was performed to demonstrate that the deletion/insertion constructed in the plasmid was maintained in the genome of the amplified CELO AIM46 virus.

The primers used for PCR are the following:

OAIM 24: (CCGAGAATCCACCAATCGTA) (SEQ. ID NO: 1) is a sense oligo hybridizing in CELO right end (at nt 41699).

OAIM25: (CAGCGTGTCGCTATACGCAA) (SEQ. ID NO: 2) is an antisense oligo hybridizing in the CELO right end (at nt 43752).

OAIM26: (GCGATGACGAAATTCTTAGC) (SEQ. ID NO: 3) is a sense oligo hybridizing in the luciferase expression cassette.

PCR with OAIM24 and 25 should give a 2053 bp product with a wildtype CELO template and a 3422 bp product with the AIM46 template. PCR with OAIM24 and 26 should give a 958 bp product with AIM46 template and no product with wildtype CELO template.

Figure 4:
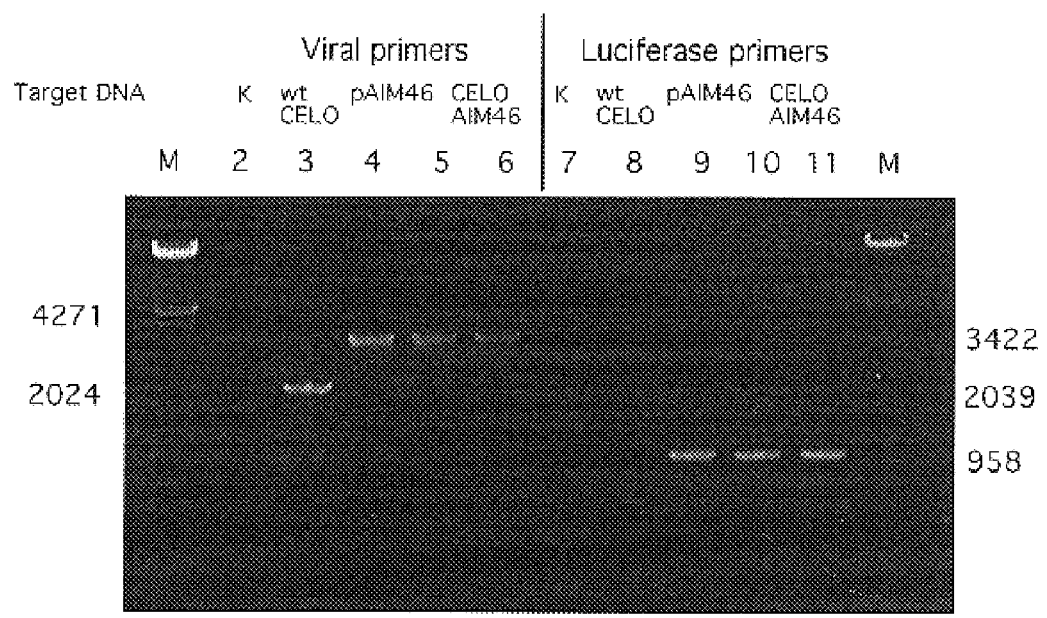

The result of the PCR analysis of wt CELO vs. CELO AIM46 is shown in FIG. 4:

Lanes marked M: marker DNA, (EcoR1/HindIII cut Lambda DNA); lanes 2 to 6: primers OAIM24+OAIM26 were used with, lane 2: irrelevant target DNA; lane 3: wt CELO DNA; lane 4: plasmid pAIM46 DNA; lane 5 and 6: DNA isolated from CELO AIM46; Lanes 7 to 11: primers OAIM24 and OAIM26were used with, lane 7: irrelevant DNA; lane 8: wt CELO DNA; lane 9: plasmid pAIM46 DNA; lanes 10 and 11: DNA isolated from CELO AIM46 DNA. DNA sizes (in base pair) are indicated for some of the marker molecules (left side ) and for the expected PCR products (right side).

As shown in FIG. 4, both the plasmid pAIM46 and DNA isolated from the virus CELO AIM46 produced the expected PCR products. Primers that span the deletion/insertion site generate the predicted PCR product of 3422 bp with pAIM46 target DNA (FIG. 4, lane 4) and with DNA derived from two CELO AIM46 preparations (FIG. 4, lanes 5 and 6)while PCR with wildtype CELO DNA produces the predicted DNA molecule of 2039 bp (FIG. 4, lane 3). Furthermore, primers that recognize the luciferase insert produce the predicted 958 bp product from DNA derived from pAIM46 or from two isolates of CELO AIM46 (FIG. 4, lanes 9–11), but not from DNA derived from wildtype CELO (FIG. 4, lane 8).

EXAMPLE 4

Immunofluorescence Analysis of CELO AIM46 vs. Wild-type CELO Replication

Luciferase data showed that CELO AIM46 can replicate in LMH cells in the absence of complementation. To analyze more directly the replication of CELO AIM46 in comparison to wildtype CELO, the two virus types were used to infect LMH cells and the progression of virus infection was monitored by immunofluorescence microscopy using a polyclonal antiserum directed against CELO capsid proteins. FIG. 5 shows the immunofluorescence, monitoring the replication of wildtype CELO vs. CELO AIM46. LMH cultures were infected at 500 particles per cell with either CELO AIM46 (upper row) or wildtype CELO (lower row). Cell samples were fixed at the indicated times post-infection and production of CELO virion proteins was monitored by immunofluorescence using an antiserum agaiNt CELO virion. For both wildtype CELO and CELO AIM46, replication is first detectable at 10 hours post-infection and the signal increases over the next 30 hours until cytopathic effect results in detachment of cells and a decline in the fluorescence signal. Thus, in a cell culture infection, CELO AIM 46 appears to replicate with kinetics that are similar to wildtype CELO.

EXAMPLE 5

Growth of CELO AIM46 in Chicken Embryos

In the initial stages of this work, LMH cells were used for cell culture propagation of CELO AIM46. Because the nature of the transformation event that established this cell line is not clear, it remains possible that the LMH cells provide some helper functions for CELO AIM46 that wildtype chicken embryonic cells might lack. This experiment should also determine if CELO AIM46 was capable of growing in chicken embryos for practical considerations: the low cost and ease of handling of embryos would facilitate production of these viruses. Equal quantities of either wildtype CELO or CELO AIM46 were injected into the allantoic cavity of 9 day old chicken embryos. After incubation at 37° C. for 4 days, the allantoic fluid was harvested and virus was purified by banding in CsCl density gradients. Yields of purified wildtype CELO ranged from 0.149 to 0.9 mg per egg (average: 0.427) mg/egg) while CELO AIM46 yields were from 0.119 to 0.828 mg per egg (average: 0.301 mg/egg; Table 3). The modifications introduced in CELO AIM46 appear to effect the growth of AIM46 in chicken embryos to only a modest extent.

EXAMPLE 6

Physical Stability of CELO AIM46

A distinctive feature of the CELO virion is physical stability, most readily measured by resistance of the virion to elevated temperatures. While mastadenoviruses such as Ad5 are inactivated by exposure to temperatures of 48° C. and higher (4, 8, 16), CELO was originally reported to be stable at 56° C. (57) and subsequent isolates of the virus have been reported with stability at higher temperatures as well as to other harsh treatments (reviewed in 39). The molecular nature of the CELO stability has not been determined. A major component of the Ad5 capsid stability, pIX, has not been identified in CELO. Perhaps hexon or other capsid components have altered sequences which allow more stable protein/protein interactions. It is likely that this stability is important in the wild for CELO virus survival in the harsh avian environment. In any case, it was of interest to determine if the CELO recombinant vector retains the stability of the wildtype CELO virion.

A recombinant adenovirus type 5 bearing a luciferase expression unit (AdLuc) and CELO AIM45 were exposed to a heat titration (30 minute exposure to defined temperatures from 42 to 68° C.). Subsequently, each sample was tested for its ability to transfer luciferase activity to either human A549 or avian CEF cells. FIG. 6 shows the immunofluorescence assays monitoring the replication of wildtype CELO vs. CELO AIM46. LMH cultures were infected at 500 particles per cell with either CELO AIM46 (upper row) or wildtype CELO (lower row). Cell samples were fixed at the indicated times post-infection and production of CELO virion proteins was monitored by immunofluorescence using an antiserum againt CELO virion.

As previously demonstrated for Ad5, the virus capsid, and thus the transduction ability of the virus is sensitive to heat (4, 8, 16). Ad5 transduction of human cells declines by a factor of more than 100 when exposed to 48° C. for 30 minutes and is inactivated at 52° C. and higher temperatures (FIG. 6). In strong contrast, CELO AIM46 transduction ability is not affected by heating at 56° C. and the virus only begins to lose activity when exposed to 60° C. for 30 minutes (FIG. 6). It was found that transduction with wildtype CELO displays similar heat stability indicating that the alterations introduced in CELO AIM46 do not significantly alter the virion's stability.

EXAMPLE 7

CELO Can Transduce a Variety of Cell Types

In considering future applications, it is of interest to determine the types of cells that can be transduced by a CELO-based vector. A panel of commonly used mammalian and chicken cell types was tested for their transducibility by CELO AIM46. For comparison, the Ad5 derivative Adluc carrying the same luciferase expression cassette was used. The results for four of these cell types are presented in FIG. 7 which shows the tropism of CELO vs. Ad5. The indicated cell types were exposed to a AdLuc or CELO AIM46 at 10000, 3000, 1000, or 300 particles per cell (see methods section for the protocol for 24 well plate). At 24 hours post-infection, luciferase activity was determined. The values are the average of three transductions with the standard deviations indicated Cells of avian origin (e.g. the chicken fibroblast line CEF38) were transduced with nearly 100-fold greater efficiency with the CELO vector than with the human AdLuc (FIG. 7). Note that CEF38 cells do not support virus replication, so the difference between the Ad5 vector and the CELO vector cannot be ascribed to an amplification associated with virus replication and must be due to primary transduction or gene expression effects. In the human cell types tested, CELO worked comparable the Ad5 vector. These include the hepatoma line HepG2, the lung epithelial carcinoma line A549 and primary human dermal fibroblast (FIG. 7). Similar results were obtained with the human carcinoma line HeLa, the murine myoblast line C2C12, and the canine epithelial line MDCK.

In conclusion, it was found that CELO AIM46 is capable of transducing avian cells approximately 100-fold more efficiently than a human Ad5 vector. Surprisingly, CELO AIM46 is also transduces mammalian cell types with efficiencies comparable to an Ad5 based vector.

EXAMPLE 8

GFP Expression from Adenovirus and CELO Vectors

The green fluorescent protein (GFP) has emerged as a useful marker for gene transfer studies. Accordingly, a CELO vector (CELO AIM53) expressing EGFP (Clontech) in the CELO AIM46 background was prepared. This vector was compared to an Ad5 vector bearing the same CMV/EGFP/βglobin expression unit. It was found that both vectors function to transfer a GFP gene in human A549 cells. The results are shown in FIG. 8, which depicts the transduction of EGFP using recombinant Ad5 or CELO vectors. The EGFP expressing adenovirus AdGFP and CELO AIM53 were used to infect human A549 cells over a range of virus/cell ratios (10 to 1000 particles per cell). At 24 hours post-infection, cells were fixed and GFP expression was monitored by fluorescence microscopy. Although immunofluorescence with GFP is not quantitative in this format, it appears that, similar to the luciferase recombinants, there are not large differences in transduction capacity between the CELO and the Ad5 EGFP viruses when transducing human A549 cells.

EXAMPLE 9

Further Deletions of the CELO Right End

A similar mutational strategy as in Example 3 was used to generate additional deletions in the right end sequences of CELO. The genome plasmid pAIM69 contains a deletion from 41523–43684, disrupting the same two open reading frames that are affected in CELO AIM46. The genome plasmid pAIM70 contains a slightly larger deletion from 40065–43684 and disrupts the same two ORFs as AIM46 and AIM 69 plus one additional ORF. Analysis was performed as outlined in Example 3, FIG. 2B, except that the right end complementing plasmid pB13.3 was used in place of the pB5.5 (FIG. 9, lanes labeled "plus right end"). Both mutant genomes included a luciferase cassette in place of the deleted sequences. pAIM69 and pAIM70 were transfected into LMH cells either alone or with a plasmid bearing the wildtype CELO right end sequences (pB13.3). Luciferase activity was obtained in lysates of the transfected cells demonstrating successful transfection. Subsequent passage of the material on fresh LMH cells revealed that both AIM69 and AIM70 were capable of generating infectious CELO particles in the absence of the intact right end sequences (FIG. 9). As shown for CELO AIM46, the two disrupted open reading frames in pAIM69 are thus dispensable for cell culture growth of CELO. The additional open reading disrupted in AIM70 is apparently also dispensable for cell culture growth.

EXAMPLE 10
Comparison of the Tropism of Adenoviruss 5 with CELO

The following cell types from various animal species were infected in order to compare the tropism of Ad5 and CELO:

MA-104 (Rhesus monkey); ED-2 (equine);
SPEV (porcine), FLU-R (porcine), WSH-R (wild boar),
KN-R1 (bovine), KMU-R (bovine); KLU-R1 (bovine).

The cell types listed above were exposed to a AdLuc or CELO AIM46 from 10,000, 3,000, 1,000, 300, 100, 30, or 10 particles per cell (see methods section for the protocol for 24 well plate). All cells were grown in Dulbecco's modifed Eagle's medium plus 10% fetal calf serum (DMEM, 2 mM glutamine, 100 IU penicillin, 100 µg/ml streptomycin and 10% (v/v) fetal calf serum, all sera were heat inactivated at 56° C. for 60 minutes). Cells were plated at $5\times10^4$ cells/well of 24 well plates approximately 18 hours before transduction. For transduction, the medium was changed to DMEM containing 2% horse serum (500 µl per well) containing the indicated virus article number. After 4 hours at 37° C., the medium was changed to DMEM/10% FCS. At 24 hours post-infection, luciferase activity was determined. The values given in FIGS. 10a–10h are the average of three transductions with the standard deviations indicated. Virus growth, purification and quantitation were done as previously described above (Example 7).

EXAMPLE 11

Recombinant protein production using a CELO AIM46 derivative

Figure 11:
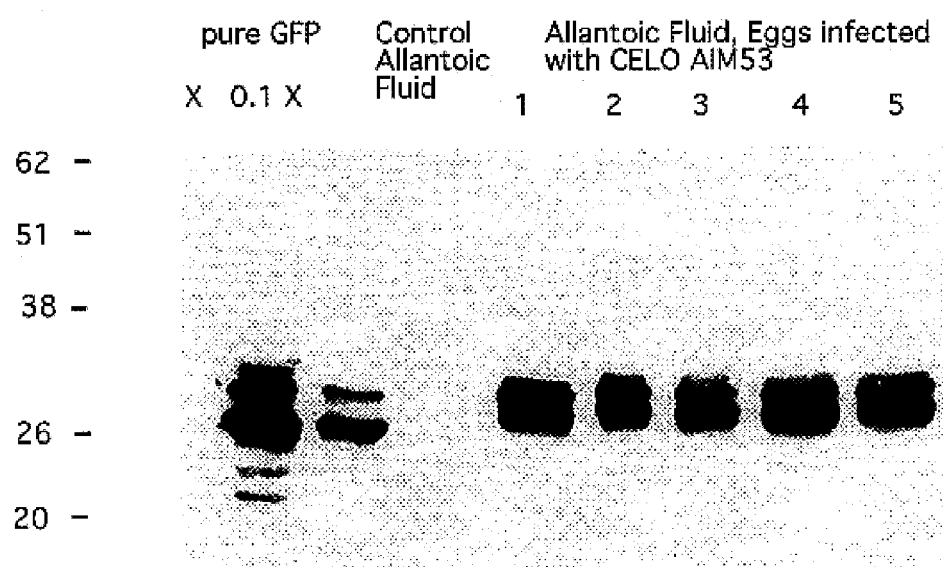

Chicken embryos (9 -days old) were infected with $4\times10^7$ particles of CELO AIM53, a CELO AIM46 derivative. After a 4 day incubation at 37 C, allantoic fluid (AF) was harvested (approximately 12 ml of AF per embryo). Aliquots of AF were resolved by SDS-PAGE, transferred to nitrocellulose and eGFP was detected by immunostaining with an antibody that recognized eGFP (Clontech), followed by ECL detection (Amersham) (FIG. 11). Reference aliquots of purified eGFP were included. Comparing the yield of eGFP in the unfractionated AF to the reference it can be calculated that 28 µl of AF contain approximately 1.25 µg of eGFP, thus 12 ml of AF would yield approximately 500 µg of eGFP. Similar quantities of eGFP were obtained from 5 separate infected embryos.

EXAMPLE 12

Figure 12:
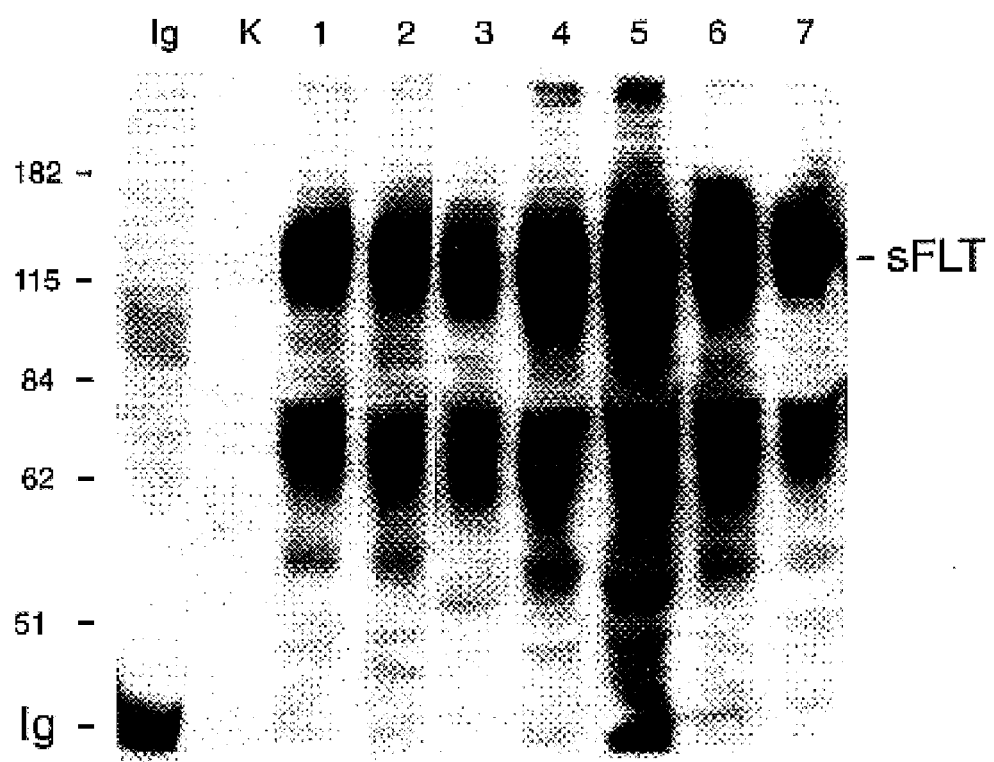

The cDNAs encoding Fc-stabilized soluble receptor constructs from sFGFR2 (66) or sFLT (sFLT; 68) were cloned between the CMV promoter and βglobin intron/polyadenylation sequence of the transfer plasmid pPM7. Subsequently, the CMV promoter/sFGFr/βglobin or CMV promoter/sFLT/βglobin fragments were introduced into PacI linearized pAIM46 using homologous recombination to produce pCELOsFGFr or pCELOsFLT. The recombination replaced the luciferase cDNA of pAIM46 with the soluble receptor cDNAs. pCELOsFGFr or pCELOsFLT were cut with SpeI to release the viral genome and transfected into LMH cells to initiate virus replication. After amplification of the viruses and purification of the viruses on CsCl gradients, aliquots of each virus ($4\times10^7$ particles) were introduced into the allantoic cavity of 9-day old chicken embryos. 4 days later the allantoic fluid was harvested (ca. 12 ml per egg). The content of Fc-stabilized soluble receptor was determined by immunoblotting using an antibody specific for the Fc domain. FIG. 12 shows the results from eggs infected with CELOsFLT. Lane Ig: 1 µg of murine Ig as standard, Lane K: 35 µl of allantoic fluid from a non-infected egg; Lanes 1–7: 35 of allantoic fluid from eggs infected with CELOsFLT; the mobilities of the immunoglobulin standard (Ig) and the approximately 120 kd sFLT molecule (sFLT) are indicated. From the standard it can be calculated that each egg contains 300–500 µg of the soluble receptor.

TABLE 1

Plasmids used in CELO recombinant construction.

| Plasmid name | CELO left end sequences | CELO right end sequences | Comments |
|---|---|---|---|
| pWü-H35 | 1–1601 | 42845–43804 | Left and right terminal CELO HindIII fragments cloned with flanking SpeI linkers in pBR327 |
| pB5.5 | 1–5503 | — | Left terminal CELO HpaI fragment in pBluescript |
| pB13.3 | — | 30502–43804 | Right terminal CELO HpaI fragment in pBluescript |
| pWüHpa | 1–5503 | 30502–43804 | Left and right terminal CELO HpaI fragments, with flanking SpeI linkers in pBR327 |
| pAIM3 | 1–5503 | 30502–30643 40064–43804 | pWüHpa derivative (removal of Asp718 fragment) |
| pAIM7 (luc*) | 1–1069 4339–5503 | 30502–30643 40064–43804 | pWüHpa derivative transfer vector for pAIM11 |
| pAIM16 (luc) | 1–2981 4339–5503 | 30502–30643 40064–43804 | pWüHpa derivative transfer vector for pAIM21 |
| pAIM22 (luc) | 1–940 2303–5503 | 30502–30643 40064–43804 | pWüHpa derivative transfer vector for pAIM25 |
| pAIM23 (luc) | 1–1069 2681–5503 | 30502–30643 40064–43804 | pWüHpa derivative transfer vector for pAIM26 |
| pAIM24 (luc) | 1–1689 2903–5503 | 30502–30643 40064–43804 | pWüHpa derivative transfer vector for pAIM27 |
| pAIM43 (luc) | 1–5503 | 30502–30643 40064–43804 | pWüHpa derivative transfer vector for pAIM45 |
| pAIM44 (luc) | 1–5503 | 30502–30643 40064–43804 | pWüHpa derivative transfer vector for pAIM46 |
| pAIM52 (EGFP) | — | — | transfer vector for homologous recombination with pAIM44 | luc* = luciferase

TABLE 2

Plasmids containing CELO variants

| CELO genome construct | Celo sequences deleted | Replication in LMH cells |
|---|---|---|
| CELO Left end | | |
| pAIM11 | 1065–4334 (3269 bp) AatII + NcoI | Defective, cannot be complemented |
| pAIM25 | 938–2300 (1362 bp) Eco47-3 | Defective, can be complemented |

TABLE 2-continued

Plasmids containing CELO variants

| CELO genome construct | Celo sequences deleted | Replication in LMH cells |
|---|---|---|
| pAIM26 | 1065–2681 (1616 bp) AatII + SphI | Defective, can be complemented |
| pAIM27 | 1687–2900 (1213 bp) PmaCI | Defective, can be complemented |
| pAIM21 | 2981–4334 (1353 bp) StyI | Defective, cannot be complemented |
| CELO Right end | | |
| pAIM45 | 33358–43684 (10326 bp) EcoRV | Defective, cannot be complemented |
| pAIM46 | 41731–43684 (1953 bp) EcoRV | Replication competent |
| pAIM53 | | |
| pAIM69 | 41523–43684 (2161 bp) PvuII-EcoRV | Replication competent |
| pAIM70 | 40065–43684 (3619) Asp718 + EcoRV | Replication competent |

TABLE 3

Yield of CELO virus from eggs.[1]

| Virus type | Preparation # | yield (mg CsCl purified virus)[2] | number of eggs | virus per egg (mg) | average yield per egg (mg) |
|---|---|---|---|---|---|
| wildtype CELO | 1 | 1.80 | 2 | 0.90 | 0.427 |
| wildtype CELO | 2 | 0.496 | 2 | 0.248 | |
| wildtype CELO | 3 | 0.345 | 2 | 0.173 | |
| wildtype CELO | 4 | 1.33 | 2 | 0.665 | |
| wildtype CELO | 5 | 5.96 | 40 | 0.149 | |
| CELO AIM 46 | 1 | 1.66 | 2 | 0.828 | 0.301 |
| CELO AIM 46 | 2 | 0.133 | 1 | 0.133 | |
| CELO AIM 46 | 3 | 0.247 | 1 | 0.247 | |
| CELO AIM 46 | 4 | 0.618 | 2 | 0.309 | |
| CELO AIM 46 | 5 | 0.340 | 2 | 0.170 | |
| CELO AIM 46 | 6 | 0.237 | 2 | 0.119 | |

Notes
[1]Wildtype CELO or CELO AIM46 ($8 \times 10^8$ particles in 100 μl of HBS) were injected into the allantoic cavity of 9 day old chicken embryos. After 4 days of incubation at 37° C., allantoic fluid was harvested and virus was purified by banding in CsCl density gradients as previously described (9).
[2]The virus yield is expressed as purified virus protein. Protein was measured by Bradford assay using bovine serum albumin as a standard.

REFERENCES

1. Baker, A., M. Saltik, H. Lehrmann, I. Killisch, V. Mautner, G. Lamm, G. Christofori, and M. Cotten. 1997. Gene Therapy 4: 773–782.
2. Bett A. J., W. Haddara, L. Prevec, F. L. Graham. 1994. Proc Natl Acad Sci USA 91:8802–8806
3. Boussif O., F. Lezoualc'h, M. A. Zanta, M. D. Mergny, D. Scherman, B. Demeneix, and J.-P.Behr. 1995. Proc. Natl. Acad. Sci. U S A. 92: 7297–7301.
4. Caravokyri, C. and K. N. Leppard. 1995. J. Virol. 69: 6627–6633.
5. Chartier C., E. Degryse, M. Gantzer, A. Dieterle, A. Pavirani, and M. Mehtali. 1996. J. Virol. 70: 4805–4810.
6. Chiocca, S., R. Kurzbauer, G. Schaffner, A. Baker, V. Mautner, and M. Cotten. 1996. J. Virol. 70: 2939–2949.
7. Chiocca, S., A. Baker, and M. Cotten. 1997. J. Virol. 71: 3168–3177.
8. Colby, W. W. and T. Shenk. 1981. J. Virol. 39: 977–980.
9. Cotten, M., E. Wagner, K. Zatloukal, and M. L. Birnstiel. 1993. J. Virol. 67:3777–3785.
10. Cowen, B., B. W. Calnek, N. A. Menendez and R. F. Ball. 1978. Avian Diseases 22: 459–470.
11. Crouzet J., L. Naudin, C. Orsini, E. Vigne, L. Ferrero, A. Le Roux, P. Benoit, M. Latta, C, Torrent, D. Branellec, P. Denefle, J. F. Mayaux, M. Perricaudet, and P. Yeh, 1997. Proc Natl Acad Sci USA 94: 1414–1419.
12. DeGregori J., G. Leone, A. Miron, L. Jakoi, and J. R. Nevins. 1997. Proc Natl Acad Sci USA 94: 7245–7250.
13. Degryse, E. 1996. Gene 170: 45–50.
14. de Wet J. R., K. V. Wood, M. DeLuca , D. R. Helinski, and S. Subramani. 1987. Mol Cell Biol 7:725–737.
15. Fisher K. J., H. Choi, J. Burda, S. J. Chen, and J. M. Wilson 1996. Virology 217: 11–22.
16. Ghosh-Choudhury, G., Y. Haj-Ahmad, and F. L. Graham. 1987. EMBO J. 6: 1733–1739.
17. Gillen, J. R., D. K. Willis, and A. J. Clark. 1974. in Mechanisms in Genetic Recombination (R. F. Greil, ed.) Plenum, New York, pp123–135.
18. Gluzman, Y., H. Reichl, and D. Solnick, 1982. Helper-free adenovirus type 5 vectors. p187–192. in Y. Gluzman (ed.) Eukaryotic Viral Vectors. Cold Spring Harbor Laboratory Press, Cold Spring Harbor, N.Y.
19. Graham F. L., J. Smiley, W. C. Russell, and R. Nairn. 1977. J. Gen. Virol. 36:59–74.
20. Grubb B. R., R. J. Pickles, H. Ye, J. R. Yankaskas, R. N. Vick, J. F. Engelhardt, J. M. Wilson, L. G. Johnson, and R. C. Nature 371: 802–806.
21. Hardy S., M. Kitamura, T. Harris-Stansil, Y. Dai, M. L. Phipps. 1997. J Virol 71: 1842–1849.
22. Hay, R. T., N. D. Stow, and I. M. McDougall. 1984. J. Mol. Biol. 175: 493–510.
23. He T. C., S. Zhou, L. T. da Costa, J. Yu, K. W. Kinzler, and B. A. Vogelstein. 1998. Proc Natl Acad Sci USA 95:2509–2514.
24. Hess, M., A. Cuzange, R. W. H. Ruigrok, J. Chroboczek and B. Jacrot. 1995. J. Mol. Biol. 252:379–385.
25. Horwitz, M. S. 1996. Adenoviruses. pp2149–2171 in Fields Virology, Third Edition. edited by B. N. Fields, D. M. Knipe, P. M. Howley et al., Lippincott-Raven Publishers, Philidelphia.
26. Imler J. L., C. Chartier, A. Dieterle, D. Dreyer, M. Mehtali, and A. Pavirani. 1995. Gene Ther. 2: 263–268.
27. Kawaguchi T., K. Nomura, Y. Hirayama, T. Kitagawa. 1987. Cancer Res. 47: 4460–4464.
28. Karlsson S., R. K. Humphries, Y. Gluzman, and A. W. Nienhuis. 1985. Proc Natl Acad Sci USA 82: 158–162.
29. Khatri A., Z. Z. Xu, and G. W. Both. 1997. Virology 239: 226–237.
30. Klonjkowski B., P. Gilardi-Hebenstreit, J. Hadchouel, V. Randrianarison, S. Boutin, P. Yeh, M. Perricaudet, and E. J. Kremer. 1997. Hum. Gene Ther. 8: 2103–2115
31. Kovesdi I., D. E. Brough, J. T. Bruder, and T. J. Wickham. 1997. Curr. Opin. Biotechnol. 8: 583–589
32. Kumar-Singh R., and J. S. Chamberlain. 1996. Hum Mol Genet 5: 913–921.
33. Laver, W. G., H. B. Younghusband and N. G. Wrigley. 1971. Virology 45: 598–614.
34. Lemay P., M. L. Boudin, M. Milleville, and P. Boulanger. 1980. Virology 101: 131–143.

35. Li, P., A. J. D. Bellett and C. R. Parish. 1984a. J. Gen. Virol. 65: 1803–1815.
36. Li, P., A. J. D. Bellett and C. R. Parish. 1984b. J. Virol. 52: 638–649.
37. Li, P., A. J. D. Bellett and C. R. Parish. 1984c. J. Virol. 65: 1817–1825.
38. Lieber A., C. Y. He, I. Kirillova, and M. A. Kay. 1996. J Virol 70: 8944–8960.
39. McFerran, J. B. and B. M. Adair. 1977. Avian Pathology 6: 189–217.
40. Mittal S. K., L. Prevec, F. L. Graham, and L. A. Babiuk. 1995. J. Gen. Virol. 76:93–102.
41. Miyake S., M. Makimura, Y. Kanegae, S. Harada, Y. Sato, K. Takamori, C. Tokuda, and I. Saito. 1996. Proc Natl Acad Sci USA 93: 1320–1324.
42. Oliner, J. D., K. W. Kinzler, and B. Vogelstein. 1993. Nucleic Acids Research 21: 5192–5197.
43. Parks R. J., L. Chen, M. Anton, U. Sankar, M. A. Rudnicki, F. L. Graham. 1996. Proc Natl Acad Sci USA 93: 13565–13570.
44. Petersson, U. and R. J. Roberts. 1986. Adenovirus gene expression and replication: a historical review. in DNA Tumor Viruses: Control of Gene Expression and Replication pp 37–57. Cold Spring Harbor Laboratory Press, Cold Spring Harbor, N.Y.
45. Plank C., K. Zatloukal, M. Cotten, K. Mechtler, and E. Wagner. 1992. Bioconjugate Chemistry. 3: 533–539.
46. Polyak K., Y. Xia, J. L. Zweier, K. W. Kinzler, and B. Vogelstein. 1997. Nature 389: 300–305.
47. Robinson A. J., H. B. Younghusband, and A. J. Bellett. 1973. Virology 56:54–69.
48. Schaack J., S. Langer, X. Guo. 1995. J Virol. 69: 3920–3923.
49. Shenk, T. 1995. Group C adenovirus as vectors for gene therapy.pp 2111–2148 in Viral Vectors (eds. M. G. Kaplitt and A. D. Loewy) pp. 43–54. Academic Press, San Diego.
50. Shenk, T. 1996. Adenoviridae: The viruses and their replication. in Fields Virology, Third Edition. edited by B. N. Fields, D. M. Knipe, P. M. Howley et al., Lippincott-Raven Publishers, Philidelphia.
51. Soberon X., L. Covarrubias, F. Bolivar. 1980. Gene 9: 287–305.
52. Van Doren K., D. Hanahan, and Y. Gluzman. 1984. J Virol . 50: 606–614.
53. Vrati S., E. S. Macavoy, Z. Z. Xu, C. Smole, D. B. Boyle, and G. W. Both. 1996b, Virology 220: 200–203.
54. Weiss R. S., S. S. Lee, B. V. Prasad, and R. T. Javier. 1997. J. Virol. 71:1857–1870.
55. Wilson C., and M. A. Kay. 1995. Nature Medicine. 1: 887–889.
56. Xu Z. Z., A. Hyatt, D. B. Boyle and G. W. Both. 1997. Virology 230: 62–71.
57. Yates, V. J. and D. E. Fry. 1957. Am. J. Vet. Res. 18: 657–660.
58. Zabner J., B. G. Zeiher, E. Friedman, and Welsh M. J. 1996. J.Virol. 70: 6994–7003.
59. Zabner J., P. Freimuth, A. Puga, A. Fabrega, and Welsh M J. 1997. J. Clin. Invest. 100: 1144–1149.
60. Zheng B., S. K. Mittal, F. L. Graham, and L. Prevec. 1994. Virus Res 31: 163–186
61. Lillehoj H. S.,and Trout J. M., 1996, Clin. Microbiol. Rev., July 9(3): 349–360
62. Taylor M. A., and Catchpole J. 1994, Appl. Parasitol, June 35(2): 73–86
63. Shirley M. W., 1992, Br. Vet. J., November 148(6): 479–499
64. Lasher H. N. and Davis V. S., 1997, Avian Dis., January 41 (1): 11–19
65. Buge S. L., Richardson E., Alipanah S., Markham P., Cheng S., Kalyan N., Miller C. J., Lubeck M., Udem S., Eldridge J., Robert-Guroff M., 1997, J Virol November;71 (11):8531–41
66. Celli G., LaRochelle W. J., Mackem S., Sharp R., Merlino G., 1998, EMBO J. March 16;17(6):1642–55
67. de Quinto S. L., Martinez-Salas E., 1998, Gene September 14;217 (1–2):51–6
68. Gerber H. P., Hillan K. J., Ryan A. M., Kowalski J., Keller G. A., Rangell L., Wright B. D., Radtke F., Aguet M., Ferrara N., 1999, Development March;126(6): 1149–59
69. Gerdts V., Jons A., Makoschey B., Visser N., Mettenleiter T. C., 1997, J Gen Virol September;78 (Pt 9):2139–46
70. Havenga M. J. E., Vogels R., Braakman E., Kroos N., Valerio D., Hagenbeek A., van Es H. H. G., 1998, Gene November 19;222(2):319–27
71. Levenson V. V., Transue E. D., Roninson I. B., 1998, Hum Gene Ther May 20;9(8):1233–6
72. Li X., Wang W., Lufkin T., 1997, Biotechniques November;23(5):874–8, 880, 882
73. Lubeck M. D., Natuk R., Myagkikh M., Kalyan N., Aldrich K., Sinangil F., Alipanah S., Murthy S. C., Chanda P. K., Nigida S. M. Jr., Markham P. D., Zolla-Pazner S., Steimer K., Wade M., Reitz M. S. Jr., Arthur L.O., Mizutani S., Davis A., Hung P. P., Gallo R. C., Eichberg J., Robert-Guroff M., 1997, Nat Med June;3(6): 651–8
74. Plank C., Zatloukal K., Cotten M., Mechtler K., and Wagner E., 1992, Bioconjugate Chemistry. 3: 533–539.
75. Robbins A. K., Watson R. J., Whealy M. E., Hays W. W., Enquist L. W., 1986, J Virol May;58(2):339–47
76. Schreurs C., Mettenleiter T. C., Zuckermann F., Sugg N., Ben-Porat T., 1988, J Virol July;62(7):2251–7
77. Vermeulen A. N., 1998, Int J Parasitol July;28(7): 1121–30
78. Talsma H., et al., 1997, Int. J. of Pharmaceutics 157, 233–238

What is claimed is:

1. Recombinant fowl adenovirus type 1 (CELO) virus or CELO virus DNA, characterized in that the genome contains a deletion consisting essentially of nucleotides 41,731–43,684 of the wild type CELO virus genome.

2. The recombinant CELO virus or CELO virus DNA of claim 1, characterized in that it contains, in addition to the deletion defined in claim 1, a complete or partial deletion or an insertion of foreign DNA within the region spanning nucleotides 794–1330.

3. The recombinant CELO virus DNA of claim 1 contained on a plasmid that can be replicated in procaryotic or eucaryotic cells.

4. The recombinant CELO virus or CELO virus DNA of claim 1, characterized in that it contains a foreign DNA insertion in place of the deletion.

5. The recombinant CELO virus or CELO virus DNA of claim 4, characterized in that the foreign DNA encodes an antigen derived from an animal pathogen.

6. The recombinant CELO virus or CELO virus DNA of claim 5, characterized in that the pathogen is avian.

7. The recombinant CELO virus or CELO virus DNA of claim 4, characterized in that the foreign DNA encodes a human protein.

8. The recombinant CELO virus or CELO virus DNA of claim 7, characterized in that the foreign DNA encodes a therapeutically active protein.

9. The recombinant CELO virus or CELO virus DNA of claim 8, characterized in that the foreign DNA encodes an immunostimulatory protein.

10. The recombinant CELO virus or CELO virus DNA of claim 9, characterized in that the immunostimulatory protein is a cytokine.

11. The recombinant CELO virus or CELO virus DNA of claim 7, characterized in that the foreign DNA encodes a tumor antigen or an immunogenic fragment thereof.

12. The recombinant CELO virus or CELO virus DNA of claim 8, characterized in that the foreign DNA encodes a protein that modulates angiogenesis.

13. The recombinant CELO virus or CELO virus DNA of claim 7, characterized in that the foreign DNA encodes an antigen derived from a human pathogen.

14. A method for producing the recombinant CELO virus of claim 1, characterized in that the deletion and optionally insertion are carried out on a plasmid-borne CELO virus DNA and that the recombinant CELO virus DNA is introduced into a host that supports virus replication.

15. Recombinant fowl adenovirus type 1 (CELO) virus or CELO virus DNA, characterized in that the genome contains a deletion consisting essentially of nucleotides 41,523–43,684 of the wild type CELO virus genome.

16. The recombinant CELO virus or CELO virus DNA of claim 15, characterized in that it contains, in addition to the deletion defined in claim 15, a complete or partial deletion or an insertion of foreign DNA within the region spanning nucleotides 794–1330.

17. The recombinant CELO virus DNA of claims 15 contained on a plasmid that can be replicated in procaryotic or eucaryotic cells.

18. The recombinant CELO virus or CELO virus DNA of claim 15, characterized in that it contains a foreign DNA insertion in place of the deletion.

19. The recombinant CELO virus or CELO virus DNA of claim 18, characterized in that the foreign DNA encodes an antigen derived from an animal pathogen.

20. The recombinant CELO virus or CELO virus DNA of claim 19, characterized in that the pathogen is avian.

21. The recombinant CELO virus or CELO virus DNA of claim 18, characterized in that the foreign DNA encodes a human protein.

22. The recombinant CELO virus or CELO virus DNA of claim 21, characterized in that the foreign DNA encodes a therapeutically active protein.

23. The recombinant CELO virus or CELO virus DNA of claim 22, characterized in that the foreign DNA encodes an immunostimulatory protein.

24. The recombinant CELO virus or CELO virus DNA of claim 23, characterized in that the immunostimulatory protein is a cytokine.

25. The recombinant CELO virus or CELO virus DNA of claim 21, characterized in that the foreign DNA encodes a tumor antigen or an immunogenic fragment thereof.

26. The recombinant CELO virus or CELO virus DNA of claim 22, characterized in that the foreign DNA encodes a protein that modulates angiogenesis.

27. The recombinant CELO virus or CELO virus DNA of claim 21, characterized in that the foreign DNA encodes an antigen derived from a human pathogen.

28. A method for producing the recombinant CELO virus of claim 15, characterized in that the deletion and optionally insertion are carried out on a plasmid-borne CELO virus DNA and that the recombinant CELO virus DNA is introduced into a host that supports virus replication.

29. Recombinant fowl adenovirus type 1 (CELO) virus or CELO virus DNA, characterized in that the genome contains a deletion consisting essentially of nucleotides 41,002–43,684 of the wild type CELO virus genome.

30. The recombinant CELO virus or CELO virus DNA of claim 29, characterized in that it contains, in addition to the deletion defined in claim 29, a complete or partial deletion or an insertion of foreign DNA within the region spanning nucleotides 794–1330.

31. The recombinant CELO virus DNA of claim 29 contained on a plasmid that can be replicated in procaryotic or eucaryotic cells.

32. The recombinant CELO virus or CELO virus DNA of claim 29, characterized in that it contains a foreign DNA insertion in place of the deletion.

33. The recombinant CELO virus or CELO virus DNA of claim 29, characterized in that the foreign DNA encodes an antigen derived from an animal pathogen.

34. The recombinant CELO virus or CELO virus DNA of claim 33, characterized in that the pathogen is avian.

35. The recombinant CELO virus or CELO virus DNA of claim 29, characterized in that the foreign DNA encodes a human protein.

36. The recombinant CELO virus or CELO virus DNA of claim 35, characterized in that the foreign DNA encodes a therapeutically active protein.

37. The recombinant CELO virus or CELO virus DNA of claim 36, characterized in that the foreign DNA encodes an immunostimulatory protein.

38. The recombinant CELO virus or CELO virus DNA of claim 37, characterized in that the immunostimulatory protein is a cytokine.

39. The recombinant CELO virus or CELO virus DNA of claim 35, characterized in that the foreign DNA encodes a tumor antigen or an immunogenic fragment thereof.

40. The recombinant CELO virus or CELO virus DNA of claim 36, characterized in that the foreign DNA encodes a protein that modulates angiogenesis.

41. The recombinant CELO virus or CELO virus DNA of claims 29, characterized in that the foreign DNA encodes an antigen derived from a human pathogen.

42. A method for producing the recombinant CELO virus claim 29, characterized in that the deletion and optionally insertion are carried out on a plasmid-borne CELO virus DNA and that the recombinant CELO virus DNA is introduced into a host that supports virus replication.

43. Recombinant fowl adenovirus type 1 (CELO) virus or CELO virus DNA, characterized in that the genome contains a deletion consisting essentially of nucleotides 40,065–43,684 of the wild type CELO virus genome.

44. The recombinant CELO virus or CELO virus DNA of claim 43, characterized in that it contains, in addition to the deletion defined in claim 43, a complete or partial deletion or an insertion of foreign DNA within the region spanning nucleotides 794–1330.

45. The recombinant CELO virus DNA of claim 43 contained on a plasmid that can be replicated in procaryotic or eucaryotic cells.

46. The recombinant CELO virus or CELO virus DNA of claim 43, characterized in that it contains a foreign DNA insertion in place of the deletion.

47. The recombinant CELO virus or CELO virus DNA of claim 46, characterized in that the foreign DNA encodes an antigen derived from an animal pathogen.

48. The recombinant CELO virus or CELO virus DNA of claim 47, characterized in that the pathogen is avian.

49. The recombinant CELO virus or CELO virus DNA of claim 47, characterized in that the foreign DNA encodes a human protein.

50. The recombinant CELO virus or CELO virus DNA of claim 49, characterized in that the foreign DNA encodes a therapeutically active protein.

51. The recombinant CELO virus or CELO virus DNA of claim 50, characterized in that the foreign DNA encodes an immunostimulatory protein.

52. The recombinant CELO virus or CELO virus DNA of claim 51, characterized in that the immunostimulatory protein is a cytokine.

53. The recombinant CELO virus or CELO virus DNA of claim 49, characterized in that the foreign DNA encodes a tumor antigen or an immunogenic fragment thereof.

54. The recombinant CELO virus or CELO virus DNA of claim 50, characterized in that the foreign DNA encodes a protein that modulates angiogenesis.

55. The recombinant CELO virus or CELO virus DNA of claim 49, characterized in that the foreign DNA encodes an antigen derived from a human pathogen.

56. A method for producing the recombinant CELO virus of claim 43, characterized in that the deletion and optionally insertion are carried out on a plasmid-borne CELO virus DNA and that the recombinant CELO virus DNA is introduced into a host that supports virus replication.

* * * * *